United States Patent
AlSinan et al.

(10) Patent No.: US 12,050,297 B2
(45) Date of Patent: Jul. 30, 2024

(54) METHOD AND SYSTEM FOR DETERMINING ENERGY-BASED BRITTLENESS

(71) Applicants: SAUDI ARABIAN OIL COMPANY, Dhahran (SA); King Abdullah University of Science and Technology, Thuwal-Jeddah (SA)

(72) Inventors: Salma AlSinan, Dhahran (SA); Eduardo David Gramajo Silva, Thuwal-Jeddah (SA); Juan Carlos Santamarina, Thuwal-Jeddah (SA); Thomas Finkbeiner, Thuwal-Jeddah (SA)

(73) Assignees: SAUDI ARABIAN OIL COMPANY, Dhahran (SA); King Abdullah University of Science and Technology, Thuwal-Jeddah (SA)

( * ) Notice: Subject to any disclaimer, the term of this patent is extended or adjusted under 35 U.S.C. 154(b) by 993 days.

(21) Appl. No.: 17/018,463

(22) Filed: Sep. 11, 2020

(65) Prior Publication Data

US 2022/0082727 A1    Mar. 17, 2022

(51) Int. Cl.
*G01V 20/00* (2024.01)
*E21B 43/267* (2006.01)
(Continued)

(52) U.S. Cl.
CPC ............ *G01V 20/00* (2024.01); *E21B 43/267* (2013.01); *E21B 49/00* (2013.01); *E21B 49/02* (2013.01);
(Continued)

(58) Field of Classification Search
CPC ......... C09K 8/62; E21B 43/267; E21B 49/00; E21B 49/003; E21B 49/005; E21B 49/02;
(Continued)

(56) References Cited

U.S. PATENT DOCUMENTS 2,311,430 A    2/1943 Beno
2,801,540 A    8/1957 Rondeau
(Continued)

FOREIGN PATENT DOCUMENTS

AU    2013246743 B2    6/2016
CA    2 869 912 A1    10/2013
(Continued)

OTHER PUBLICATIONS

Noufal, Abdelwahab, Germay, Christophe, Lhomme, Tanguy, Hegazy, Gehad, and Thomas Richard. "Enhanced Core Analysis Workflow for the Geomechanical Characterization of Reservoirs in a Giant Offshore Field, Abu dhabi.", Nov. 2015. doi: https://doi.org/10.2118/177412-MS (Year: 2015).*
(Continued)

*Primary Examiner* — Lisa M Caputo
*Assistant Examiner* — Eric Sebastian Von Wald
(74) *Attorney, Agent, or Firm* — Osha Bergman Watanabe & Burton LLP

(57) ABSTRACT

A method may include determining an energy factor based on scratch test data and ultrasonic wave data regarding a geological region of interest. The method may further include determining an amount of inelastic energy regarding the geological region of interest using triaxial compression data and rock property data. The method may further include determining a tensile strength regarding the geological region of interest using Brazilian test data. The method may further include generating a geomechanical model regarding the geological region of interest using the energy factor and the amount of inelastic energy. The geomechanical model may include various brittleness values for the geological region of interest. The method may further include determining an injection fluid pressure to induce a hydraulic fracture at a predetermined location in the geological region (Continued)

of interest using the geomechanical model, the tensile strength, and fracture plane roughness data.

14 Claims, 10 Drawing Sheets

(51) Int. Cl.
*E21B 49/00* (2006.01)
*E21B 49/02* (2006.01)
*G01N 3/10* (2006.01)
*G01N 15/08* (2006.01)
*G01N 33/24* (2006.01)
*G01V 1/50* (2006.01)

(52) U.S. Cl.
CPC .............. *G01N 3/10* (2013.01); *G01N 15/082* (2013.01); *G01N 33/24* (2013.01); *G01V 1/50* (2013.01); *E21B 2200/20* (2020.05); *G01N 2203/0019* (2013.01); *G01V 2210/1429* (2013.01); *G01V 2210/60* (2013.01)

(58) Field of Classification Search
CPC .... E21B 2200/20; E21B 43/26; E21B 47/002; E21B 49/006; E21B 47/0025; E21B 7/00; G01N 3/10; G01N 15/082; G01N 33/24; G01N 33/241; G01N 2203/0014; G01N 2203/0016; G01N 2203/0017; G01N 2203/0019; G01N 2203/0026; G01N 2203/0098; G01N 2223/04; G01N 2223/419; G01N 23/046; G01N 3/08; G01N 3/56; G01V 99/005; G01V 1/42; G01V 1/46; G01V 1/48; G01V 1/50; G01V 2210/1429; G01V 2210/60; G01V 2210/646; G01V 2210/663; G06F 2111/10; G06F 30/20; G06G 7/48
See application file for complete search history.

(56) References Cited

U.S. PATENT DOCUMENTS

| | | | |
|---|---|---|---|
| 3,934,468 A | 1/1976 | Brieger | |
| 3,961,524 A | 6/1976 | de la Cruz | |
| 3,969,929 A | 7/1976 | Shaw et al. | |
| 3,992,928 A | 11/1976 | Thoms | |
| 4,075,885 A | 2/1978 | Handy et al. | |
| 4,149,409 A | 4/1979 | Serata | |
| 4,444,058 A | 4/1984 | Ratigan | |
| 4,461,171 A | 7/1984 | de la Cruz | |
| 4,510,799 A | 4/1985 | Overmier | |
| 4,539,851 A | 9/1985 | Lutenegger | |
| 4,557,147 A | 12/1985 | Rohde et al. | |
| 4,686,653 A | 8/1987 | Staron et al. | |
| 4,697,650 A | 10/1987 | Fontenot | |
| 4,773,259 A | 9/1988 | Handy | |
| 4,806,153 A | 2/1989 | Sakai et al. | |
| 4,914,591 A | 4/1990 | Warren et al. | |
| 5,165,274 A | 11/1992 | Thiercelin | |
| 5,207,104 A | 5/1993 | Enderlin | |
| 5,323,648 A | 6/1994 | Peltier et al. | |
| 5,670,711 A | 9/1997 | Detournay et al. | |
| 6,655,220 B1 | 12/2003 | Reiffsteck | |
| 7,404,456 B2 | 7/2008 | Weaver et al. | |
| 7,921,730 B2 | 4/2011 | Tan | |
| 8,141,419 B2 | 3/2012 | Tchakarov et al. | |
| 8,234,912 B2 | 8/2012 | Suarez-Rivera et al. | |
| 8,571,799 B2 | 10/2013 | Suarez-Rivera et al. | |
| 9,238,966 B2 | 1/2016 | Pitcher et al. | |
| 9,411,071 B2 | 8/2016 | Gray et al. | |
| 9,482,087 B2 | 11/2016 | Badri et al. | |
| 9,606,036 B2 | 3/2017 | Su et al. | |
| 10,132,162 B2 | 11/2018 | Neale et al. | |
| 10,519,769 B2 | 12/2019 | Havens et al. | |
| 10,544,673 B2 | 1/2020 | Lakings et al. | |
| 10,689,972 B1* | 6/2020 | Zhao | E21B 47/06 |
| 11,726,074 B2* | 8/2023 | Martysevich | G01N 33/24 |
| | | | 73/818 |
| 2004/0011119 A1 | 1/2004 | Jardret et al. | |
| 2004/0237640 A1 | 12/2004 | Meister et al. | |
| 2009/0164128 A1 | 6/2009 | Tchakarov et al. | |
| 2009/0260415 A1 | 10/2009 | Suarez-Rivera et al. | |
| 2009/0260883 A1 | 10/2009 | Suarez-Rivera et al. | |
| 2010/0051347 A1 | 3/2010 | Tchakarov et al. | |
| 2010/0191471 A1 | 7/2010 | de Reynal | |
| 2013/0262069 A1 | 10/2013 | Leonard | |
| 2014/0352949 A1 | 12/2014 | Amendt et al. | |
| 2016/0069182 A1 | 3/2016 | Neale et al. | |
| 2017/0009575 A1 | 1/2017 | Liu et al. | |
| 2017/0058669 A1 | 3/2017 | Lakings et al. | |
| 2017/0067337 A1 | 3/2017 | Havens et al. | |
| 2017/0275989 A1 | 9/2017 | Lakings et al. | |
| 2018/0106147 A1 | 4/2018 | Akings et al. | |
| 2018/0292300 A1 | 10/2018 | Su et al. | |
| 2018/0334897 A1 | 11/2018 | Samuel et al. | |
| 2019/0145251 A1* | 5/2019 | Johnson | E21B 43/26 |
| | | | 166/250.1 |
| 2020/0003052 A1 | 1/2020 | Benoit et al. | |
| 2021/0017844 A1* | 1/2021 | Perez | E21B 41/00 |

FOREIGN PATENT DOCUMENTS

| | | |
|---|---|---|
| CN | 102066984 A | 5/2011 |
| CN | 102967883 A | 3/2013 |
| CN | 103122762 A | 5/2013 |
| CN | 103256046 A | 8/2013 |
| CN | 103344705 A | 10/2013 |
| CN | 103969121 A | 8/2014 |
| CN | 103982178 A | 8/2014 |
| CN | 104268377 A | 1/2015 |
| CN | 104314563 A | 1/2015 |
| CN | 104345339 A | 2/2015 |
| CN | 104406849 A | 3/2015 |
| CN | 104407381 A | 3/2015 |
| CN | 104453873 A | 3/2015 |
| CN | 104564042 A | 4/2015 |
| CN | 104569344 A | 4/2015 |
| CN | 104570128 A | 4/2015 |
| CN | 104632173 A | 5/2015 |
| CN | 103344705 B | 6/2015 |
| CN | 104677734 A | 6/2015 |
| CN | 103122762 B | 7/2015 |
| CN | 104865124 A | 8/2015 |
| CN | 105182421 A | 12/2015 |
| CN | 105203639 A | 12/2015 |
| CN | 103982178 B | 1/2016 |
| CN | 105221141 A | 1/2016 |
| CN | 105277671 A | 1/2016 |
| CN | 105445440 A | 3/2016 |
| CN | 105527652 A | 4/2016 |
| CN | 105545294 A | 5/2016 |
| CN | 105547855 A | 5/2016 |
| CN | 105675635 A | 6/2016 |
| CN | 105221141 B | 8/2016 |
| CN | 105865955 A | 8/2016 |
| CN | 105547855 B | 10/2016 |
| CN | 106248494 A | 12/2016 |
| CN | 104406849 B | 1/2017 |
| CN | 104407381 B | 1/2017 |
| CN | 106323749 A | 1/2017 |
| CN | 106323760 A | 1/2017 |
| CN | 106337682 A | 1/2017 |
| CN | 104502971 B | 2/2017 |
| CN | 106368687 A | 2/2017 |
| CN | 106383053 A | 2/2017 |
| CN | 106547034 A | 3/2017 |
| CN | 106568919 A | 4/2017 |
| CN | 106644736 A | 5/2017 |
| CN | 106872260 A | 6/2017 |
| CN | 106896410 A | 6/2017 |
| CN | 106908322 A | 6/2017 |
| CN | 104865124 B | 10/2017 |

(56) References Cited

FOREIGN PATENT DOCUMENTS

| | | | |
|---|---|---|---|
| CN | 107290219 A | 10/2017 | |
| CN | 104564042 B | 12/2017 | |
| CN | 105277671 B | 12/2017 | |
| CN | 107656310 A | 2/2018 | |
| CN | 105527652 B | 3/2018 | |
| CN | 107957487 A | 4/2018 | |
| CN | 105203639 B | 8/2018 | |
| CN | 108363110 A | 8/2018 | |
| CN | 108519281 A | 9/2018 | |
| CN | 106547034 B | 11/2018 | |
| CN | 106569266 B | 11/2018 | |
| CN | 108827774 A | 11/2018 | |
| CN | 106248494 B | 3/2019 | |
| CN | 108446431 B | 3/2019 | |
| CN | 106908322 B | 4/2019 | |
| CN | 109655909 A | 4/2019 | |
| CN | 107656310 B | 6/2019 | |
| CN | 110006738 A | 7/2019 | |
| CN | 110146374 A | 8/2019 | |
| CN | 110186755 A | 8/2019 | |
| CN | 106323749 B | 9/2019 | |
| CN | 106368687 B | 10/2019 | |
| CN | 110320571 A | 10/2019 | |
| CN | 106872260 B | 11/2019 | |
| CN | 110455661 A | 11/2019 | |
| CN | 110552690 A | 12/2019 | |
| CN | 110726608 A | 1/2020 | |
| GB | 2522945 A | 8/2015 | |
| GB | 2545144 B | 4/2019 | |
| IN | 104502971 A | 4/2015 | |
| KR | 101415196 B1 | 7/2014 | |
| KR | 101415198 B1 | 8/2014 | |
| KR | 101415199 B1 | 8/2014 | |
| WO | 03/087778 A1 | 10/2003 | |
| WO | 2009/129083 A1 | 10/2009 | |
| WO | 2012/166111 A1 | 12/2012 | |
| WO | 2014/205402 A1 | 12/2014 | |
| WO | 2017/044978 A1 | 3/2017 | |
| WO | 2017/214316 A1 | 12/2017 | |

OTHER PUBLICATIONS

S.K. Kourkoulis, Ch. F. Markides, P.E. Chatzistergos, The Brazilian disc under parabolically varying load: Theoretical and experimental study of the displacement field, International Journal of Solids and Structures, vol. 49, Issues 7-8, 2012, pp. 959-972, ISSN 0020-7683. (Year: 2012).*

Coates, D.F. and R.C. Parsons, "Experimental Criteria for Classification of Rock Substances", International Journal of Rock Mechanics Mining Sciences, Pergamon Press Ltd., vol. 3, Issue 3, Jul. 1966, pp. 181-189 (9 pages).

Gong, Q.M. and J. Zhao, "Influence of rock brittleness on TBM penetration rate in Singapore granite", Tunnelling and Underground Space Technology, ScienceDirect, Elsevier Ltd., vol. 22, Sep. 2006, pp. 317-324 (8 pages).

Hajiabdolmajid, V. et al., "Mobilised strength components in brittle failure rock", Géotechnique, vol. 53, No. 3, 2003, pp. 327-336 (10 pages).

Holt, R.M. et al., "A shaly look at brittleness", ARMA 11-366, American Rock Mechanics Association, Jun. 2011 (10 pages).

Hucka, V. and B. Das, "Brittleness Determination of Rocks by Different Methods", International Journal of Rock Mechanics and Mining Sciences & Geomechanics Abstracts, Pergamon Press, vol. 11, 1974, pp. 389-392 (4 pages).

Jarvie, Daniel M. et al., "Unconventional shale-gas systems: The Mississippian Barnett Shale of north-central Texas as one model for thermogenic shale-gas assessment", AAPG Bulletin, The American Association of Petroleum Geologists, vol. 91, No. 4, Apr. 2007, pp. 475-499 (25 pages).

Jin, Xiaochun et al., "Fracability Evaluation in Shale Reservoirs—An Integrated Petrophysics and Geomechanics Approach", SPE 168589, Society of Petroleum Engineers, Feb. 2014 (14 pages).

Luan, Xinyuan et al., "Laboratory Measurements of Brittleness Anisotropy in Synthetic Shale with Different Cementation", SEG Denver 2014 Annual Meetings, SEG, pp. 3005-3009 (5 pages).

Morrow, C.A. et al., "The effect of mineral bond strength and absorbed water on fault gouge frictional strength", Geophysical Research Letters, American Geophysical Union, vol. 27, No. 6, Mar. 2000, pp. 815-818 (4 pages).

Mullen, Mike et al., "A Composite Determination of Mechanical Rock Properties for Stimulation Design (What to Do When You Don't Have a Sonic Log)", SPE 108139, Society of Petroleum Engineers, Apr. 2007 (13 pages).

Rickman, Rick et al., "A Practical Use of Shale Petrophysics for Stimulation Design Optimization: All Shale Plays Are Not Clones of the Barnett Shale", SPE 115258, Society of Petroleum Engineers, Sep. 2008 (11 pages).

Sun, S.Z. et al., "Integrated Prediction of Shale Oil Reservoir Using Pre-Stack Algorithms for Brittleness and Fracture Detection", IPTC 17048, International Petroleum Technology Conference, Mar. 2013 (8 pages).

Tarasov, Boris and Yves Potvin, "Universal criteria for rock brittleness estimation under triaxial compression", International Journal of Rock Mechanics & Mining Sciences, SciVerse ScienceDirect, Elsevier Ltd., vol. 59, Jan. 2013, pp. 57-69 (13 pages).

Wang, Fred P. and Julia F. W. Gale, "Screening Criteria for Shale-Gas Systems", Gulf Coast Association of Geological Societies Transactions, vol. 59, 2009, pp. 779-793 (15 pages).

Walles, Frank, "A New Method to Help Identify Unconventional Targets for Exploration and Development Through Integrative Analysis of Clastic Rock Property Fields", Houston Geological Society Bulletin, Oct. 2004, pp. 35-36; 41; 43; 45-49 (8 pages).

Yagiz, Saffet, "Assessment of brittleness using rock strength and density with punch penetration test", Tunnelling and Ungerground Space Technology, ScienceDirect, Elevier Ltd., vol. 24, Jun. 2008, pp. 66-74 (9 pages).

Yang, Yi et al., "Comparison of Brittleness Indices in Organic-rich Shale Formations", ARMA 13-403, American Rock Mechanics Association, Jun. 2013 (7 pages).

Altindag, R., "The evaluation of rock brittleness concept on rotary blast hole drills", The Journal of South African Institute of Mining and Metallurgy, Jan./Feb. 2002, pp. 61-66 (6 pages).

Nygård, Runar et al., "Brittle-ductile transition, shear failure and leakage in shales and mudrocks", Marine and Petroleum Geology, Elsevier Ltd, vol. 23, Oct. 2005, pp. 201-212 (12 pages).

Guo, Zhiqi et al., "Exploring the effect of fractures and microstructure on brittleness index in the Barnett Shale", SEG Las Vegas 2012 Annual Meeting, Sep. 2012 (5 pages).

Chen, Jiaojiao et al., "The construction of shale rock physics effective model and prediction of rock brittleness", SEG Denver 2014 Annual Meeting, SEG, 2014, pp. 2861-2865 (5 pages).

Richard, T. et al., "The scratch test as a means to measure strength of sedimentary rocks", SPE/ISRM 47196, Society of Petroleum Engineers, Inc., Jul. 1998 (8 pages).

Richard, Thomas et al., "Rock strength determination from scratch tests", Engineering Geology, SciVerse ScienceDirect, Elsevier B.V., Aug. 2012, pp. 91-100 (10 pages).

Dagrain, Fabrice, "Influence of the Cutter Geometry in Rock Cutting: An Experimental Approach", A Thesis Submitted to the Faculty of the Graduate School of the University of Minnesota, Feb. 2001 (100 pages).

Demartinecourt, J.P. and Gunther E. Bauer, "The Modified Borehole Shear Device", Geotechnical Testing Journal, GTJODJ, American Society for Testing and Materials, vol. 6, No. 1, Mar. 1983, pp. 24-29 (6 pages).

De la Cruz, R. V., "Modified Borehole Jack Method for Elastic Property Determination in Rocks", Rock Mechanics, Springer-Verlag, vol. 10, 1978, pp. 221-239 (19 pages).

Zoeller, W.A., "Analysis of Rock Properties from Drilling Response", SPWLA Fifteenth Annual Logging Symposium, The Analysts., Inc., Jun. 1974 (18 pages).

Zoeller, William A., "The Drilling Porosity Log 'DPL'", Spe 3066, American Institute of Mining, Metallurgical, and Petroleum Engineers, Inc., 1970 (8 pages).

(56) References Cited

OTHER PUBLICATIONS

Ratigan, Joe Lawrence, "A Statistical Fracture Mechanics Approach to the Strength of Brittle Rock", LBL-13286, Ph. D Thesis, Lawrence Berkeley Laboratory and Department of Civil Engineering, Jun. 1981 (104 pages).
Detournay, E. and A. H-D. Cheng, "Poroelastic Response of a Borehole in a Non-hydrostatic Stress Field", International Journal of Rock Mechanics and Mining Sciences & Geomechanical Abstracts, Pergamon Press plc, vol. 25, No. 3, 1988, pp. 171-182 (12 pages).
Dai, Sheng et al., "Coda Wave Analysis to Monitor Processes in Soils", Journal of Geotechnical and Geoenvironmental Engineering, ASCE, vol. 139, No. 9, Sep. 2013, pp. 1504-1511 (8 pages).
Meng, Fanzhen et al., "Evaluation Methodology of Brittleness of Rock Based on Post-Peak Stress-Strain Curves", Rock Mechanics and Rock Engineering, CrossMark, Springer-Verlag Wien, vol. 48, Dec. 2014, pp. 1787-1805 (19 pages).
International Search Report and Written Opinion issued in Application No. PCT/US2021/049764, mailed on Jan. 10, 2022 (18 pages).
Manriquez et al.; "A novel approach to quantify reservoir pressure along the horizontal section and to optimize multistage treatments and spacing between hydraulic fractures", Journal of Petroleum Science and Engineering; vol. 149; Jan. 20, 2017; pp. 579-590 (12 pages).
Li et al.; "A Multiscale Framework for the Simulation of the Anisotropic Mechanical Behavior of Shale", International Journal for Numerical and Analytical Methods in Geomechanics; vol. 41; Aug. 2016 (51 pages).
Hernandez-Uribe et al.; "Assessment of Mudrock Brittleness with Micro-scratch Testing", Rock Mechanics and Rock Engineering; vol. 50; Jul. 18, 2017; pp. 2849-2860 (12 pages).
Ye et al.; "Brittleness Evaluation in Shale Gas Reservoirs and Its Influence on Fracability", Energies; vol. 13; Issue 2; Jan. 13, 2020; pp. 1-22 (22 pages).
Hou et al.; "Brittleness Evaluation of Shale Based on the Brazilian Splitting Test", Geofluids; vol. 2018; Apr. 16, 2018; pp. 1-11 (11 pages).
Hou et al.; "Analysis of hydraulic fracture initiation and propagation in deep shale formation with high horizontal stress difference", Journal of Petroleum Science and Engineering, vol. 170; Nov. 2018; pp. 231-243 (13 pages).

* cited by examiner

METHOD AND SYSTEM FOR DETERMINING ENERGY-BASED BRITTLENESS

BACKGROUND

Natural fractures present in subsurface formations are discontinuities representing a surface or zone of mechanical failure in the formation. In particular, fractures may be formed over geological time as a result of movements and deformations within the subsurface rock, and continue to form as a result of microseismic events. Fracture prediction is one of the more challenging problems in reservoir characterization. Fracture distributions are related to various factors such as intrinsic rock mechanic properties as well as movements and deformation of rock layers due to different tectonic stages.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method that includes determining, by a computer processor, an energy factor based on scratch test data and ultrasonic wave data regarding a geological region of interest. The method further includes determining, by the computer processor, an amount of inelastic energy regarding the geological region of interest using triaxial compression data and rock property data. The method further includes determining, by the computer processor, a tensile strength regarding the geological region of interest using Brazilian test data. The method further includes generating, by the computer processor, a geomechanical model regarding the geological region of interest using the energy factor and the amount of inelastic energy. The geomechanical model includes various brittleness values for the geological region of interest. The method further includes determining, by the computer processor, an injection fluid pressure to induce a hydraulic fracture at a predetermined location in the geological region of interest using the geomechanical model, the tensile strength, and fracture plane roughness data.

In general, in one aspect, embodiments relate to a system that includes a logging system coupled to various logging tools and a drilling system coupled to the logging system. The system further includes a reservoir simulator that includes a computer processor. The reservoir simulator is coupled to the logging system and the drilling system. The reservoir simulator determines an energy factor based on scratch test data and ultrasonic wave data regarding a geological region of interest. The reservoir simulator determines an amount of inelastic energy regarding the geological region of interest using triaxial compression data and rock property data. The reservoir simulator determines determining tensile strength regarding the geological region of interest using Brazilian test data. The reservoir simulator generates a geomechanical model regarding the geological region of interest using the energy factor and the amount of inelastic energy. The geomechanical model includes various brittleness values for the geological region of interest. The reservoir simulator determines an injection fluid pressure to induce a hydraulic fracture at a predetermined location in the geological region of interest using the geomechanical model, the tensile strength, and fracture plane roughness data.

In general, in one aspect, embodiments relate to a non-transitory computer readable medium storing instructions executable by a computer processor. The instructions determine an energy factor based on scratch test data and ultrasonic wave data regarding a geological region of interest. The instructions determine an amount of inelastic energy regarding the geological region of interest using triaxial compression data and rock property data. The instructions determine a tensile strength regarding the geological region of interest using Brazilian test data. The instructions generate a geomechanical model regarding the geological region of interest using the energy factor and the amount of inelastic energy. The geomechanical model includes various brittleness values for the geological region of interest. The instructions determine an injection fluid pressure to induce a hydraulic fracture at a predetermined location in the geological region of interest using the geomechanical model, the tensile strength, and fracture plane roughness data.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
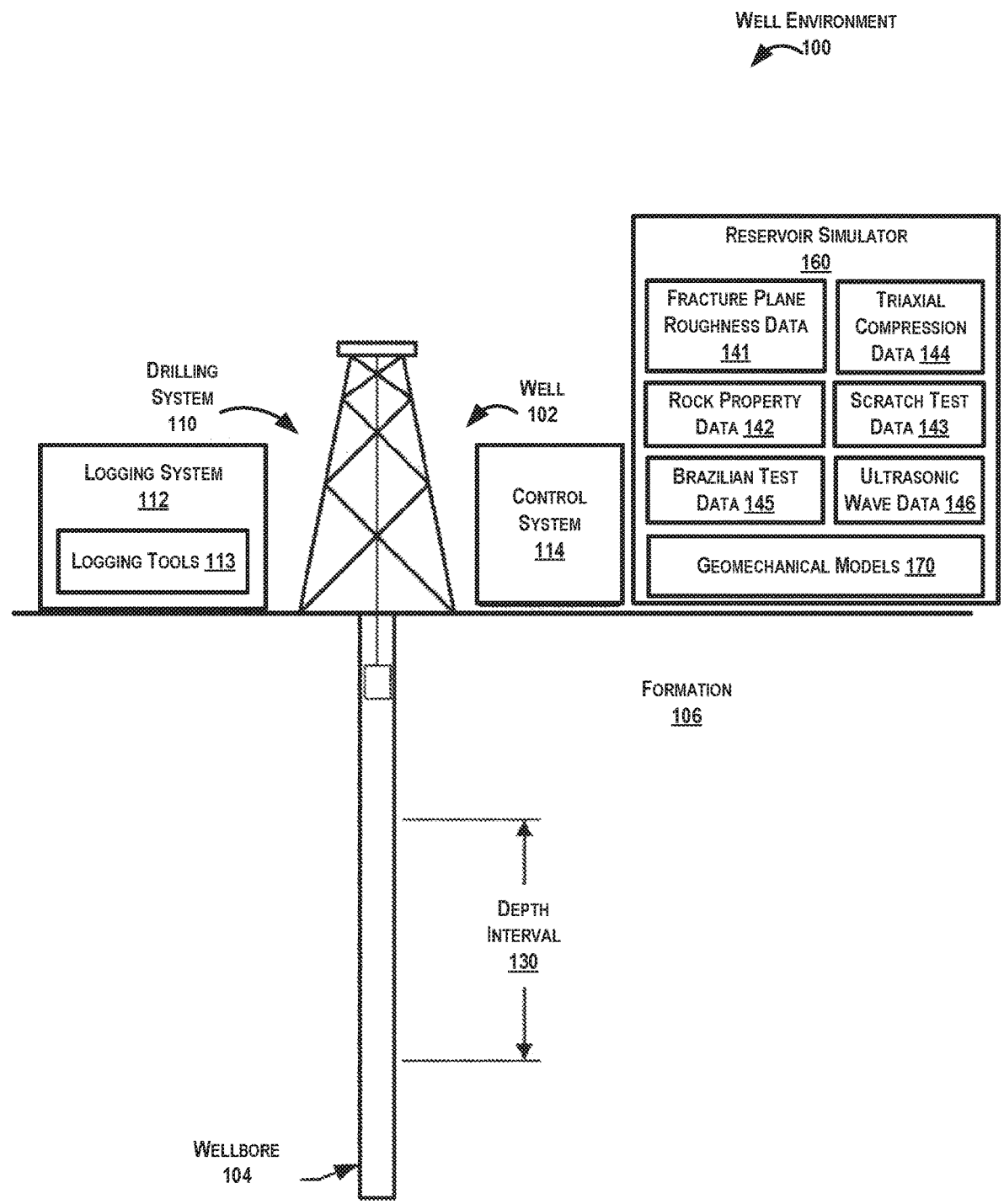
FIGS. 1 and 2 show systems in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the disclosure include systems and methods for performing an energy-based brittleness characterization of one or more geological regions. In particular, different types of data are obtained using different tasks in order to generate a geomechanical model that describes various brittleness values as well as use the geomechanical model to analyze intrinsic anisotropy effects (e.g., fabrics and layers) of a geological region. For example, a geomechanical model may be used to determine tensile strength, fracture propagation, and fracture/proppant interaction at the different bedding angle orientations within a geological region.

Furthermore, some embodiments include performance of two tasks that include obtaining laboratory measurements to constrain general rock properties and laboratory triaxial compression measurements to constrain rock stiffness, yield, and ultimate strength. These two tasks may be used to determine a specific energy (i.e., elastic and inelastic energy levels) within rock specimens for a geological region. In another task, well site measurements (such as well logs) are obtained from scratch tests and ultrasonic wave velocity measurements that are analyzed using Coda Wave interferometry. A reservoir simulator may use these well site measurements to determine a computed strength asymptote and a dynamic Young's Modulus asymptote from well-log p-wave velocities, for example. Thus, these well site measurements may be inputs into determining one or more energy factors, which offers basic energy data for evaluating failure behavior inside rock specimens at different confining pressures. Finally, fracture plane roughness data and tensile strength measurements may be used in connection with a geomechanical model to determine a hydraulic stimulation treatment, e.g., the amount of pressure required to induce a hydraulic fracture in a geological region.

Accordingly, some embodiments provide precise asymptotic values of stiffness and peak strength as a function of deformation and mineralogical composition. By quantifying inelastic energy and elastic energy in connection with energy factors, various energy variations may define brittleness values within a geomechanical model for unconventional/tight reservoirs to identify areas for hydraulic stimulation. As such, methods and systems of the disclosure may determine brittle-ductile transition zones in unconventional/tight reservoirs as well as anisotropic influences on tensile strength and fracture evolution.

Turning to FIG. 1, FIG. 1 shows a schematic diagram in accordance with one or more embodiments. As shown in FIG. 1, FIG. 1 illustrates a well environment (100) that may include a well (102) having a wellbore (104) extending into a formation (106). The wellbore (104) may include a bored hole that extends from the surface into a target zone of the formation (106), such as a reservoir. The formation (106) may include various formation characteristics of interest, such as formation porosity, formation permeability, density, resistivity, water saturation, free water level (FWL), and the like. Porosity may indicate how much space exists in a particular rock within an area of interest in the formation (106), where oil, gas, and/or water may be trapped. Permeability may indicate the ability of liquids and gases to flow through the rock within the area of interest. Resistivity may indicate how strongly rock and/or fluid within the formation (106) opposes the flow of electrical current. For example, resistivity may be indicative of the porosity of the formation (106) and the presence of hydrocarbons. More specifically, resistivity may be relatively low for a formation that has high porosity and a large amount of water, and resistivity may be relatively high for a formation that has low porosity or includes a large amount of hydrocarbons. Water saturation may indicate the fraction of water in a given pore space.

Keeping with FIG. 1, the well environment (100) may include a drilling system (110), a logging system (112), a control system (114), and a reservoir simulator (160). The drilling system (110) may include a drill string, drill bit, a mud circulation system and/or the like for use in boring the wellbore (104) into the formation (106). The control system (114) may include hardware and/or software for managing drilling operations, maintenance operations, and/or stimulation treatment operations. For example, the control system (114) may include one or more programmable logic controllers (PLCs) that include hardware and/or software with functionality to control one or more processes performed by the drilling system (110). Specifically, a programmable logic controller may control valve states, fluid levels, pipe pressures, warning alarms, and/or pressure releases throughout a drilling rig. In particular, a programmable logic controller may be a ruggedized computer system with functionality to withstand vibrations, extreme temperatures, wet conditions, and/or dusty conditions, for example, around a drilling rig. Without loss of generality, the term "control system" may refer to a drilling operation control system that is used to operate and control the equipment, a drilling data acquisition and monitoring system that is used to acquire drilling process and equipment data and to monitor the operation of the drilling process, or a drilling interpretation software system that is used to analyze and understand drilling events and progress.

Turning to the reservoir simulator (160), a reservoir simulator (160) may include hardware and/or software with functionality for storing and analyzing well logs, core specimen data, seismic data, and/or other types of data to generate and/or update one or more geomechanical models. While the reservoir simulator (160) is shown at a well site, in some embodiments, the reservoir simulator (160) may be remote from a well site. In some embodiments, the reservoir simulator (160) is implemented as part of a software platform for the control system (114). The software platform may obtain data acquired by the drilling system (110) and logging system (112) as inputs, which may include multiple data types from multiple sources. The software platform may aggregate the data from these systems (110, 112) in real time for rapid analysis. In some embodiments, the control system (114), the logging system (112), and/or the reservoir simulator (160) may include a computer system that is similar to the computer system (1302) described below with regard to FIG. 13 and the accompanying description.

The logging system (112) may include one or more logging tools (113), such as a nuclear magnetic resonance (NMR) logging tool and/or a resistivity logging tool, for use in generating well logs of the formation (106). For example, a logging tool may be lowered into the wellbore (104) to acquire measurements as the tool traverses a depth interval (130) (e.g., a targeted reservoir section) of the wellbore (104). The plot of the logging measurements versus depth may be referred to as a "log" or "well log". Well logs may provide depth measurements of the well (104) that describe such reservoir characteristics as formation porosity, formation permeability, resistivity, water saturation, and the like. The resulting logging measurements may be stored and/or processed, for example, by the control system (114), to generate corresponding well logs for the well (102). A well log may include, for example, a plot of a logging response time versus true vertical depth (TVD) across the depth interval (130) of the wellbore (104). Similarly, an in situ scratch testing tool may be lowered into the wellbore (104) and obtain a continuous strength log across the depth interval of interest (130). Such a log would provide for this disclosure critical rock property information.

Reservoir characteristics may be determined using a variety of different techniques. For example, certain reservoir characteristics can be determined via coring (e.g., physical extraction of rock specimens) to produce core specimens and/or logging operations (e.g., wireline logging, logging-while-drilling (LWD) and measurement-while-drilling (MWD)). Coring operations may include physically extracting a rock specimen from a region of interest within the wellbore (104) for detailed laboratory analysis. For example, when drilling an oil or gas well, a coring bit may cut core plugs (or "cores" or "core specimens") from the formation (106) and bring the core plugs to the surface, and these core specimens may be analyzed at the surface (e.g., in a lab) to determine various characteristics of the formation (106) at the location where the specimen was obtained.

Turning to various coring technique examples, conventional coring may include collecting a cylindrical specimen of rock from the wellbore (104) using a core bit, a core barrel, and a core catcher. The core bit may have a hole in its center that allows the core bit to drill around a central cylinder of rock. Subsequently, the resulting core specimen may be acquired by the core bit and disposed inside the core barrel. More specifically, the core barrel may include a special storage chamber within a coring tool for holding the core specimen. Furthermore, the core catcher may provide a grip to the bottom of a core and, as tension is applied to the drill string, the rock under the core breaks away from the undrilled formation below coring tool. Thus, the core catcher may retain the core specimen to avoid the core specimen falling through the bottom of the drill string.

Turning to examples of logging techniques, multiple types of logging techniques are available for determining various reservoir characteristics. For example, nuclear magnetic resonance (NMR) logging measures the induced magnetic moment of hydrogen nuclei (i.e., protons) contained within the fluid-filled pore space of porous media (e.g., reservoir rocks). Thus, NMR logs may measure the magnetic response of fluids present in the pore spaces of the reservoir rocks. In so doing, NMR logs may measure both porosity and permeability, as well as the types of fluids present in the pore spaces. For determining permeability, another type of logging may be used that is called spontaneous potential (SP) logging. SP logging may determine the permeabilities of rocks in the formation (106) by measuring the amount of electrical current generated between drilling fluid produced by the drilling system (110) and formation water that is held in pore spaces of the reservoir rock. Porous sandstones with high permeabilities may generate more electricity than impermeable shales. Thus, SP logs may be used to identify sandstones from shales.

To determine porosity in the formation (106), various types of logging techniques may be used. For example, the logging system (112) may measure the speed that acoustic waves travel through rocks in the formation (106). This type of logging may generate borehole compensated (BHC) logs, which are also called sonic logs. In general, sound waves may travel faster through high-density shales than through lower-density sandstones. Likewise, density logging may also determine porosity measurements by directly measuring the density of the rocks in the formation (106). Furthermore, neutron logging may determine porosity measurements by assuming that the reservoir pore spaces within the formation (106) are filled with either water or oil and then measuring the amount of hydrogen atoms (i.e., neutrons) in the pores. Other types of logging are also contemplated, such as resistivity logging and dielectric logging.

Figure 2:
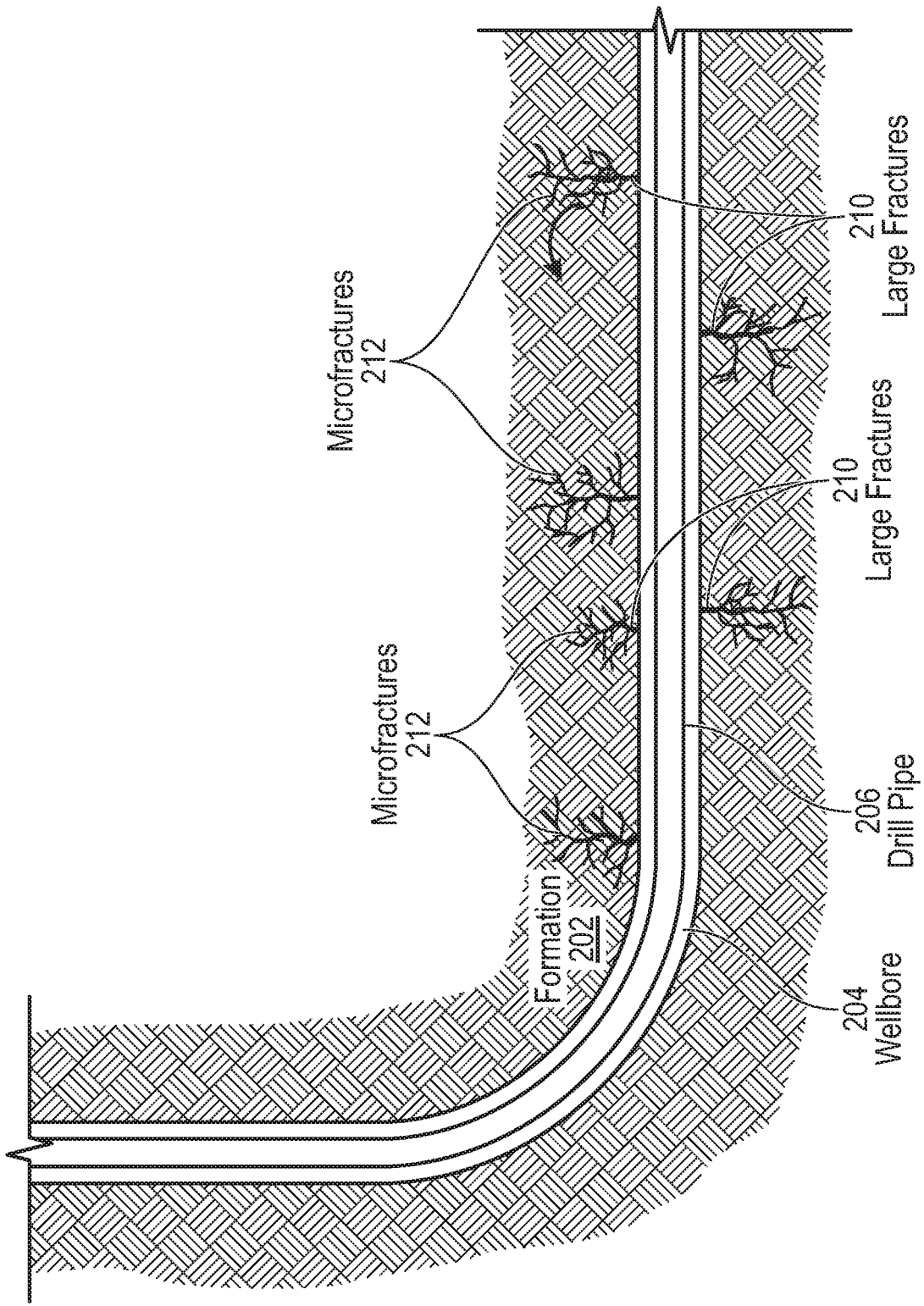

Turning to FIG. 2, FIG. 2 shows a schematic diagram in accordance with one or more embodiments. As shown in FIG. 2, FIG. 2 illustrates a stimulation treatment that forms additional microfractures (212) within a formation (202). In particular, hydrocarbon reserves may be trapped within certain low permeability formations, such as various sand, carbonate, and/or shale formations. Thus, stimulation treatments may enhance well productivity at one or more wells, where one type of stimulation treatment is hydraulic fracturing. In some embodiments, for example, hydraulic fracturing includes injecting high viscosity fluids into a wellbore at a sufficiently high injection rate so that enough pressure is produced within the wellbore to split the formation. As such, a stimulation treatment may be determined that achieves a desired height and/or length of one or more induced fractures.

With respect to FIG. 2, a wellbore (204) located within formation (202) includes drill pipe (206) that is positioned within the wellbore (204). Following a hydraulic fracturing process, for example, large fractures (210) may exist within the formation (202) and extend outward from the wellbore (204). In some embodiments, for example, an injection fluid with an activator is injected into the formation (202), where the injection fluid migrates within the large fractures (210). Upon a reaction caused by the activator, the injection fluid may produce one or more gases and heat, thereby causing the microfractures (212) to be created within the formation (202). Thus, a stimulation treatment may provide pathways for the hydrocarbon deposits trapped within the formation (202) to migrate and be recovered by a production well.

Keeping with FIG. 2, various stimulation procedures may be employed that use one or more techniques to insure that an induced fracture becomes conductive after injection ceases. For example, during acid fracturing of carbonate formations, acid based fluids may be injected into the formation to create an etched fracture and conductive channels. These conductive channels may be left open upon closure of the induced fracture. With sand or shale formations, a proppant may be included with the injection fluid such that the induced fracture remains open during or following a stimulation treatment. Likewise, in carbonate formations, a stimulation treatment may include both acid fracturing fluids and proppants. Accordingly, heat produced within a formation, acid, or aqueous water transmitted into the formation may all play a role in producing reactions causing one or more microfractures in a formation.

In some embodiments, brittleness values are determined for one or more geological regions in order to identify various sweet spots for hydraulic stimulation. In certain unconventional formations, for example, an important element that determines whether it is economically viable to develop a reservoir is the presence of one or more sweet spots in the reservoir. A sweet spot may be generally defined herein as the area within a reservoir that represents the best production or potential for production. As such, brittleness values may describe geological regions based on a lack of ductility, a destruction of internal cohesion, an ability for a rock to deform and fail with a low degree of inelastic behavior, and a rock's capability for self-sustaining fracturing. In other words, high brittleness values may correspond to geological regions that easily fracture within a formation to produce more microfractures with little plastic deformation under compression.

Based on a brittleness characterization, a reservoir simulator may identify a presence of one or more sweet spots within a formation. More specifically, a geological region may be divided between one or more brittle-ductile transitional zones (BDTZs), one or more brittle zones (BZs), and one or more ductile zones (DZs). For example, shale in a BDTZ may be characterized by semi-brittle properties with some extent of compressibility and disconnected microfractures which may not destroy the preservation conditions of shale gas. Thus, finding a BDTZ may be beneficial for development of reservoir space and shale gas preservation, where the BDTZ corresponds to an ideal depth interval or sweet spot for shale gas exploration and development.

Returning to FIG. 1, in some embodiments, a reservoir simulator determines an energy-based brittleness using rock property data (e.g., rock property data (142)), scratch test data (e.g., scratch test data (143)), triaxial compression data (e.g., triaxial compression data (144)), Brazilian test data (e.g., Brazilian test data (145)), and/or ultrasonic wave data (e.g., ultrasonic wave data (146)). For example, rock property data may describe one or more petrophysical and/or geological properties, such as mineral data (e.g., mineralogy compositions), total amount of organic carbon, porosity, pore size distribution, damage data regarding a degree of internal damage within rock specimens, etc. of a geological region. Scratch test data may describe a force distribution of a rock specimen from a geological region. Triaxial compression data may describe compression test measurements, stress data, and/or strain data that is acquired using a triaxial cell within a triaxial measurement system. Ultrasonic wave data may describe travel time velocity measurements for primary waves (i.e., p-waves) and secondary waves (i.e., s-waves). As such, ultrasonic wave data may be similar to sonic logs and borehole compensated (BHC) logs described above.

With respect to Brazilian test data, Brazilian test data may describe measurements acquired using a Brazilian disc test to determine a tensile stress distribution of a rock specimen. In some embodiments, for example, a disc-shaped specimen of rock is loaded by opposing loads at a periphery of the disc-shaped specimen in a Brazilian test apparatus. The force or pressure applied by the opposing loads may increase at a predetermined rate until a rock failure of the disc-shaped specimen occurs. More specifically, a rock failure may correspond to an initiation of cracks within the disc-shaped specimen. Thus, Brazilian test data may identify a tensile strength value where rock failure occurs.

In some embodiments, a reservoir simulator generates one or more geomechanical models (e.g., geomechanical models (170)) that describes brittleness values for one or more geological regions. In particular, a geomechanical model may describe various asymptotic parameters obtained at small and large-strain values, where the geomechanical model may be based on laboratory data and/or field data acquired at a wellsite. For example, a geomechanical model may provide information about various hydro-mechanical properties of unconventional formations. In addition, the geomechanical model may be a predictive model that determines results for stimulation treatments in unconventional formations as well future production from a new well at the reservoir. Likewise, a geomechanical model may determine fracture initiation and propagation in a particular geological region based on a particular stimulation treatment.

Furthermore, a stimulation treatment for a formation may be updated by a reservoir simulator using a geomechanical model (e.g., one of the geomechanical models (170)). For example, a reservoir simulator may use a geomechanical model to perform one or more stimulation simulations using different injection fluid pressure rates, different types of proppants, acid-based treatments and non-acid treatments, etc., to determine a desired stimulation scenario for the formation.

While FIGS. 1 and 2 shows various configurations of components, other configurations may be used without departing from the scope of the disclosure. For example, various components in FIGS. 1 and 2 may be combined to create a single component. As another example, the functionality performed by a single component may be performed by two or more components.

Figure 3:
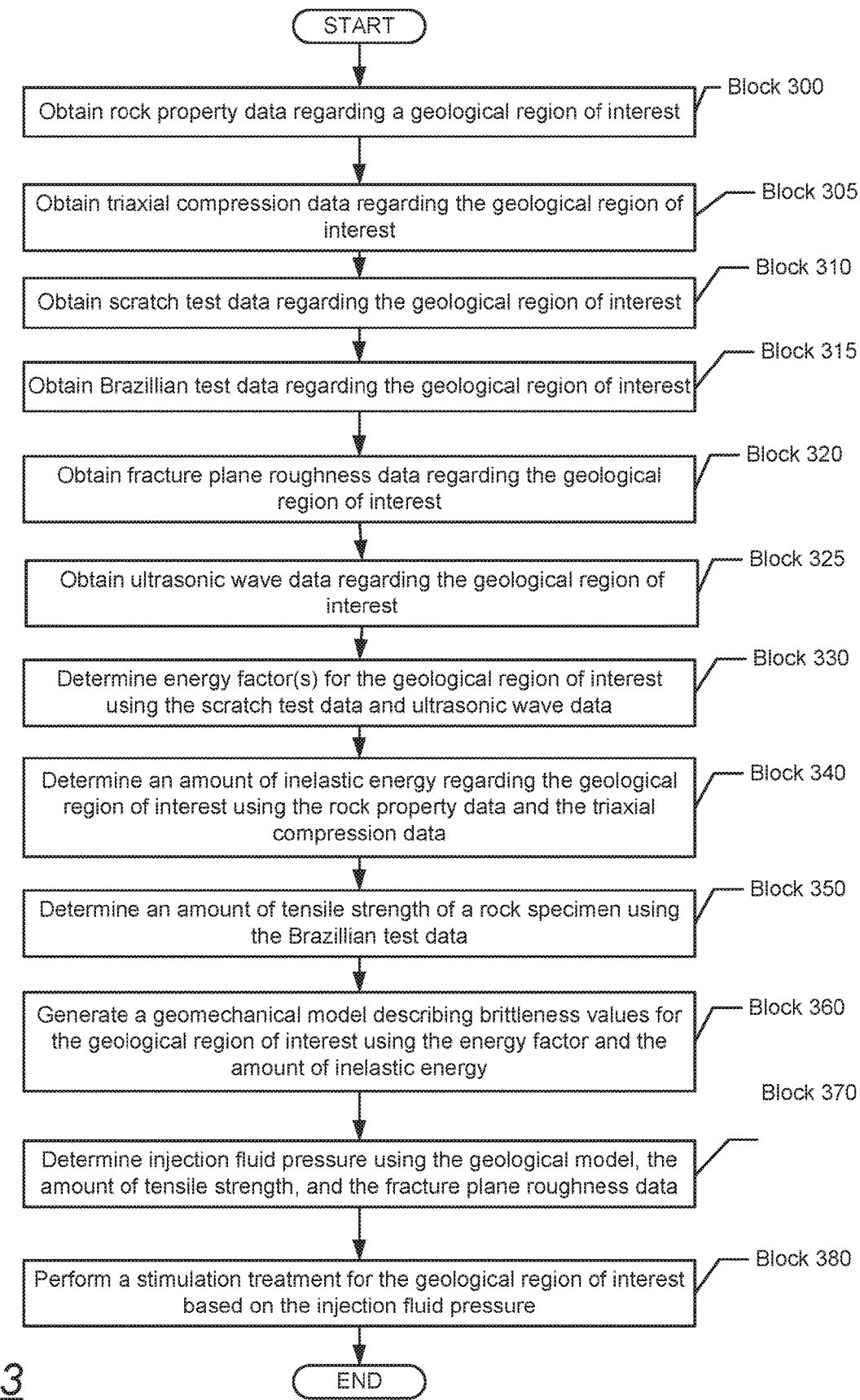
FIG. 3 shows a flowchart in accordance with one or more embodiments.

Turning to FIG. 3, FIG. 3 shows a flowchart in accordance with one or more embodiments. Specifically, FIG. 3 describes a general method for using a geomechanical model based on an energy-based brittleness. One or more blocks in FIG. 3 may be performed by one or more components (e.g., reservoir simulator (160)) as described in FIGS. 1 and 2. While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 300, rock property data are obtained regarding a geological region of interest in accordance with one or more embodiments. A geological region of interest may be a portion of a geological area or volume that includes one or more formations of interest desired or selected for analysis, e.g., for determining a location of hydrocarbons or a place for a stimulation treatment. For example, a geological region of interest may be a specific formation being analyzed for one or more new wells.

With respect to rock property data, rock property data may be obtained by laboratory characterizations and index property measurements, which provide various understandings of general rock properties. For example, rock property data may be obtained from one or more rock specimens acquired from the geological region of interest using various tests and analyses. Thus, mineralogy properties may be obtained by x-ray diffraction (XRD) or energy-dispersive x-ray spectroscopy (EDS). In some embodiments, scanning electron microscopy (SEM) are used to image a rock specimen in order to determine various rock properties. In another embodiment, an elemental analyzer performs carbon, hydrogen, nitrogen, sulfur and oxygen (CHNS/O) analyses to determine a total organic carbon composition of a rock specimen. In another embodiment, a computerized tomography (CT) scan is performed to determine internal discontinuities (e.g., damage) within rock specimens. To determine porosity and pore size distribution, a helium porosimeter and a mercury injection capillary pressure (MICP) technique may be used, respectively. Likewise, a gas adsorption technique may also be used to determine a pore size distribution. The rock property data may be similar to the rock property data (142) described above in FIG. 1 and the accompanying description.

In Block 305, triaxial compression data are obtained regarding a geological region of interest in accordance with one or more embodiments. In some embodiments, for example, triaxial compression data includes compression tests, stress/strain curves, stiffness and strength evolution, post-failure behavior, fracture pattern, and brittle/ductile response. Triaxial compression data may be acquired by placing a rock specimen into a triaxial cell within a high-pressure high-temperature triaxial system. As such, laboratory triaxial compression tests may be performed in order to understand various rock mechanics properties. The triaxial compression tests may measure rock specimen at different bedding angles (e.g., 0°, 45°, and 90°) and different confining pressures (e.g., 1, 15, 30, 60, and 100 MPa). Thus, triaxial compression data obtained using different measurement parameters may describe various anisotropic effects, elastic linear/non-linear development, plastic behavior, and post-failure schemes on the strain hardening, softening, and brittleness evolution of the geological region of interest. The triaxial compression data may be similar to the triaxial compression data (144) described above in FIG. 1 and the accompanying description.

Figure 4:
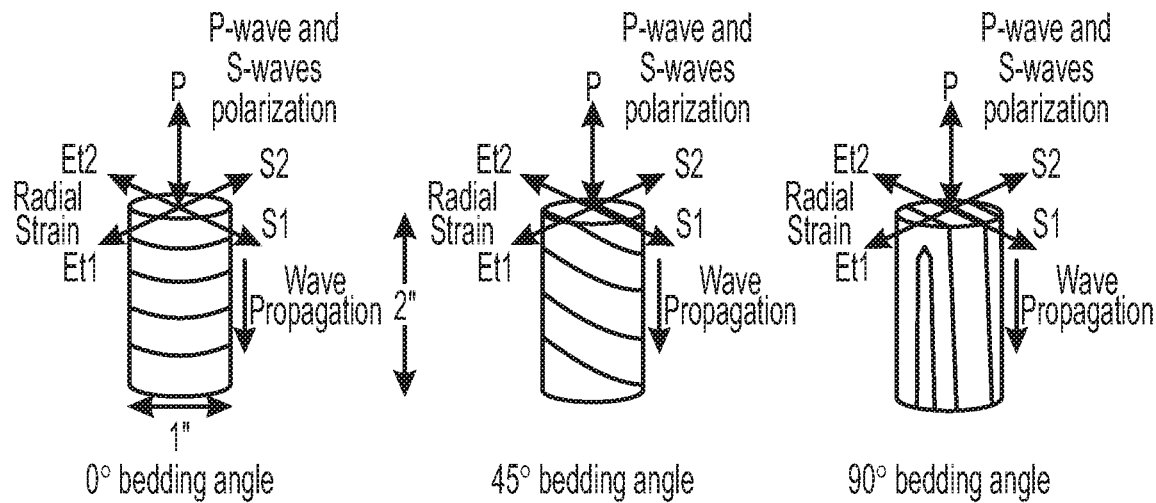
FIGS. 4, 5, 6, 7, 8, 9A, 9B, 10, 11, and 12 show examples in accordance with one or more embodiments.

Turning to FIG. 4, FIG. 4 illustrates various triaxial systems in accordance with one or more embodiments. As shown in FIG. 4, a shale core plug of 25 mm in diameter and a length to width ratio of 2:1 is analyzed as a rock specimen. In this example, the rock specimen's bedding angles, direction of major principal stress, and piezo-crystals are mounted and aligned within the top and bottom caps of the frame to enhance anisotropic comparison criteria. Thus, a triaxial system is aligned in the direction of wave propagation (i.e., p-wave and s-wave directions), the location of radial strain measurements (i.e., Et1 and Et2), and position of the axial strain displacement transducers (i.e., Ea1 and Ea2). Accordingly, the alignment of the different bedding angles is represented by continuous white lines (i.e., 0°, 45°, and 90°). The arrows show the orientation of the S2-wave together with the location of the EU radial strain measurement system. These arrows also illustrate the location of the S1-wave and the position of the Et2 radial strain system.

Figure 5:
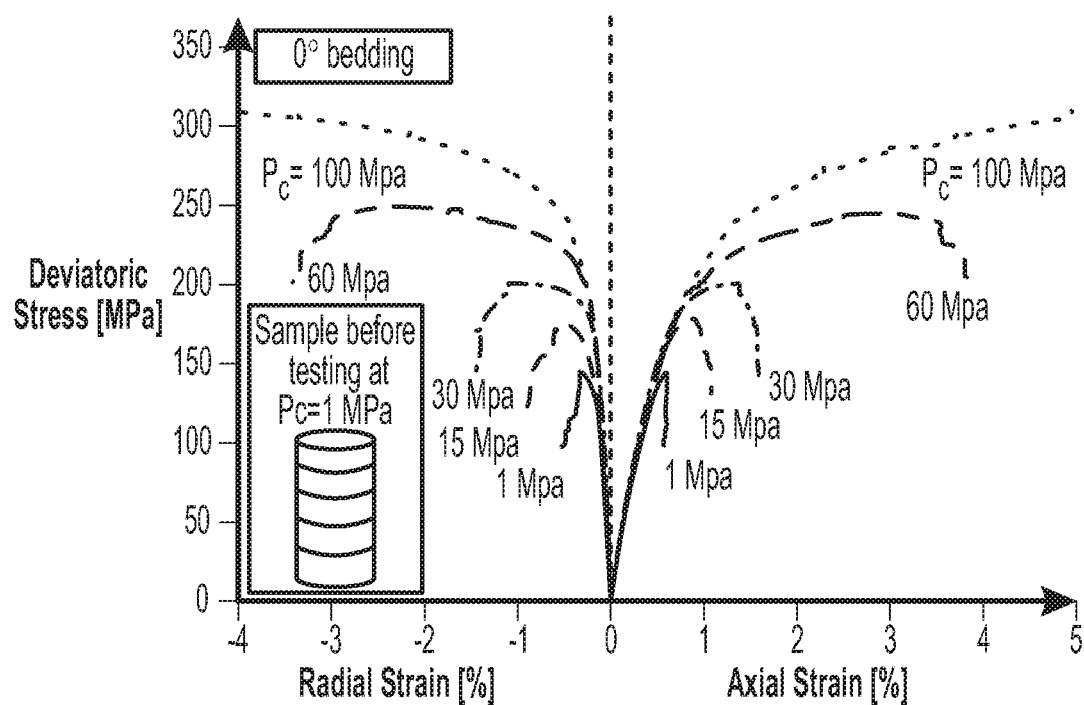

Turning to FIG. 5, FIG. 5 shows triaxial compression data in accordance with one or more embodiments. In FIG. 5, triaxial compression data provides information regarding values of the elastic moduli, peak stress thresholds that cause rock failure, and post-failure behavior for various rock specimens at a 0° bedding angle. For example, values of axial stress vs. radial and axial strain as shown in FIG. 5 may provide a causal link between the confining pressure, rock strength, and/or stiffness. In particular, the separate curves may illustrate different confining pressures corresponding to 1 MPa, 15 MPa, 30 MPa, 60 MPa, and 100 MPa.

Returning to FIG. 3, in Block 310, scratch test data are obtained regarding a geological region of interest in accordance with one or more embodiments. In some embodiments, for example, scratch test data measure various force signals that compute various strength distributions. In some embodiments, scratch test data are obtained using a scratching tool for measuring formation weaknesses at various depth intervals. In particular, a scratching tool may be pushed against a wellbore wall so as to produce scratches of various sizes and depths in the wellbore wall. Thus, the scratching tool may determine various computed strength values for different depth intervals within the wellbore. Likewise, the scratch test data may be similar to the scratch test data (143) described above in FIG. 1 and the accompanying description.

Figure 6:
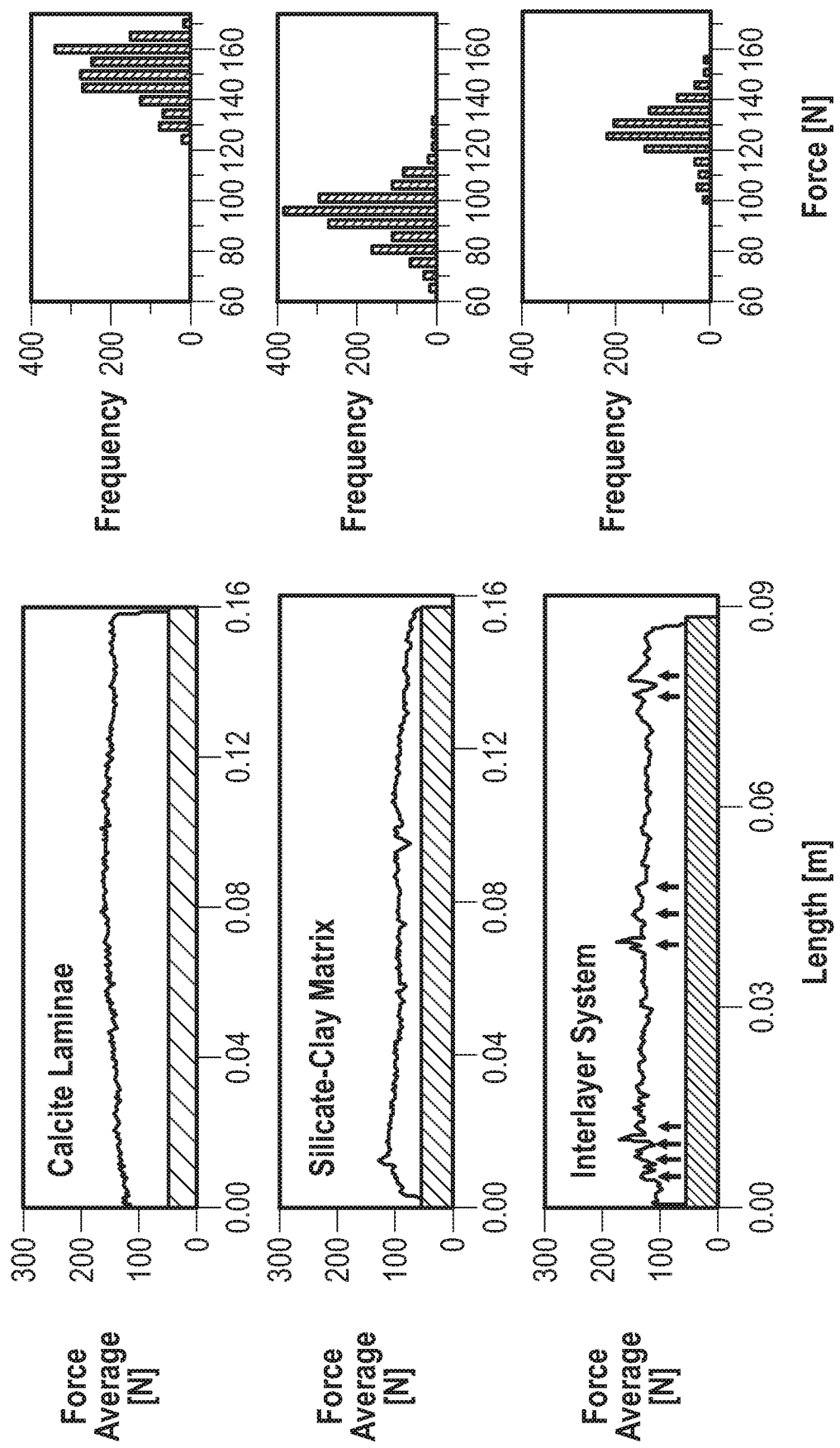

Turning to FIG. 6, FIG. 6 shows an example of scratch test data in accordance with one or more embodiments. In FIG. 6, three rectangular rock specimen types are illustrated, which include (1) calcite laminae in a top plot, (2) silicate-clay matrix in a middle plot, and (3) an interlayered area of silicate-clay matrix and calcite laminae in a bottom plot. Here, various inset force histograms show force distributions that are determined for various non-layered force variations as well as interlayer individual and bonding force variations along the rock specimens.

Returning to FIG. 3, in Block 315, Brazilian test data are obtained regarding a geological region of interest in accordance with one or more embodiments. For example, Brazilian tests may evaluate tensile strength and strain of various rock specimens to understand the impact of bedding on fracture initiation and propagation. In particular, multiple rock specimens maybe analyzed under different loading conditions to understand various bedding effects on fracture evolution and fracture initiation. Thus, the loading conditions with respect to such bedding angles may include opposing loads that are (1) parallel and perpendicular to the 45° and 90° bedding angles and/or (2) parallel to the 0° bedding angle. Brazilian test data may be similar to the Brazilian test data (145) described above in FIG. 1 and the accompanying description.

In Block 320, fracture plane roughness data are obtained regarding a geological region of interest in accordance with one or more embodiments. Fracture plane roughness data may describe a fracture's surface topography. For example, fracture plane roughness data may correspond to a surface profile of a fracture that includes such dimensions as step, curvature, and/or flatness. In some embodiments, for example, fracture plane roughness data may be acquired using a non-contact profilometer scanner, such as a profilometer that uses white light interferometry to measure a surface's roughness. Likewise, the profilometer scanner may determine a surface roughness by identifying surface deviations in a predetermined direction. Thus, fracture plane roughness data may describe various failure surfaces as well as provide fracture information regarding proppant-flow interactions with the failure surfaces.

In Block 325, ultrasonic wave data are obtained regarding a geological region of interest in accordance with one or more embodiments. In particular, initial arrivals of ultrasonic wave signals may have non-noticeable differences in travel times, even where large ratios of stress/strain values exist between ultrasonic wave signals. Accordingly, in some embodiments, Coda Wave interferometry is used to analyze initial arrival results in order to quantify minute changes between initial arrival points among ultrasonic wave signals. In particular, Coda Wave interferometry may be an ultrasound technique for detection of weak and local changes in complex inhomogeneous media. Ultrasonic waves that transmit through a rock specimen may generate slowly decaying waves, called coda waves, based on medium scattering. As such, coda wave generation may be highly repeatable such that if no change occurs in the rock specimen over time, waveforms of the coda waves may be identical. If a change occurs within the rock specimen, such as a crack from an applied load, an observable change may result in the coda waves. Thus, ultrasonic wave data may provide various elastic moduli values.

Figure 7:
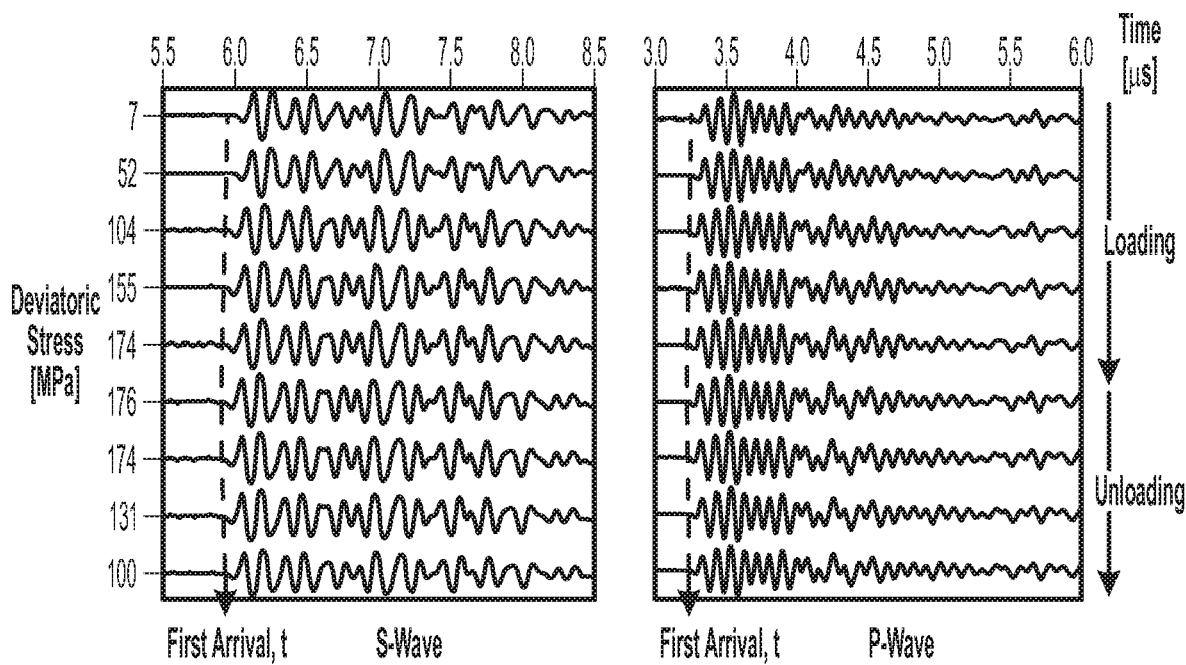
Figure 8:
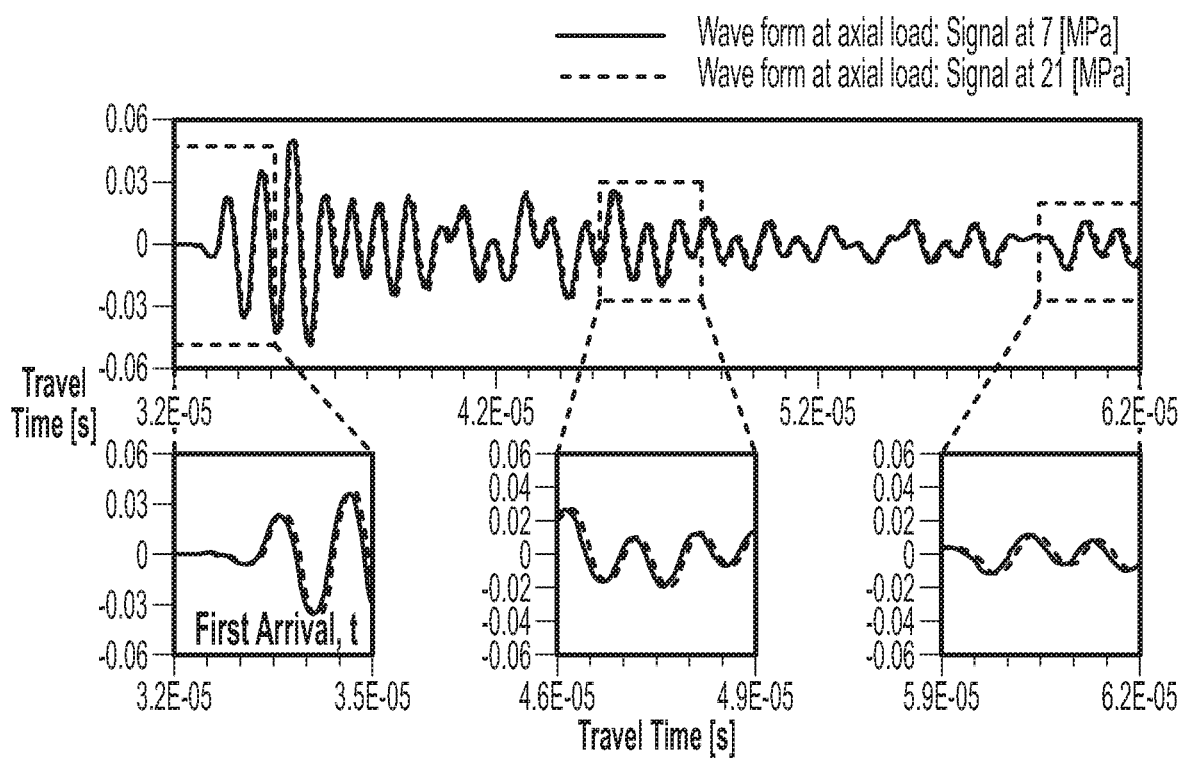

Turning to FIGS. 7 and 8, FIGS. 7 and 8 show ultrasonic wave data in accordance with one or more embodiments. For example, FIG. 7 illustrates minimal differences in initial arrival times of ultrasonic wave signals, which may provide erroneous or unprecise elastic moduli values. In contrast, FIG. 8 shows an analysis of ultrasonic wave data using Coda Wave interferometry to analyze the signals and accurately identify elastic moduli values. More specifically, two-wave signals are compared in FIG. 8 at different axial loads. As shown in FIG. 8, a solid line indicates 7 MPa of deviatoric stress and a segmented line indicates 21 MPa of deviatoric stress. Thus, ultrasonic wave data processed using Coda Wave interferometry provides a more noticeable distinction. Therefore, the Coda Wave cross-correlations stretch or shrink these two sequential signals to quantify the small variability in their initial arrival times.

Returning to FIG. 3, in Block 330, one or more energy factors are determined for a geological region of interest using scratch test data and ultrasonic wave data in accordance with one or more embodiments. In particular, scratch test data and ultrasonic wave data may be obtained from downhole well logs, such that the energy factors are based on field analogue data rather than laboratory data. The scratch test data may provide computed strength values for a geological region in order to determine a strength asymptote. In some embodiments, separate energy factors are determined from ultrasonic wave data based on p-wave measurements and s-wave measurements. For example, an energy factor $e_{FVp}$ based on p-wave measurements may be expressed by the following equation:

$$e_{FVp} = \frac{q^2}{E_D} \quad \text{Equation (1)}$$

where $q^2$ corresponds to a strength asymptote from scratch test data, and $E_D$ corresponds to a dynamic Young's modulus determined from ultrasonic wave data. Similarly, an energy factor $e_{FVs}$ based on s-wave measurements may be expressed by the following equation:

$$e_{FVs} = \frac{q^2}{G_D} \quad \text{Equation (2)}$$

where $q^2$ corresponds to the strength asymptote from scratch test data, and $G_D$ corresponds to Shear modulus determined from ultrasonic wave data. In particular, an energy factor may describe an area under a strength asymptote line for computed strength from scratch test data and an elastic moduli asymptotic line from ultrasonic wave data.

In Block 340, an amount of inelastic energy is determined regarding a geological region of interest using rock property data and triaxial compression data in accordance with one or more embodiments. For example, a laboratory specific energy may be determined using triaxial compression data and rock property data that describes the inelastic area under a compressive stress-strain curve before the peak stress threshold (see, e.g., FIG. 9A described below).

Figure 9A:
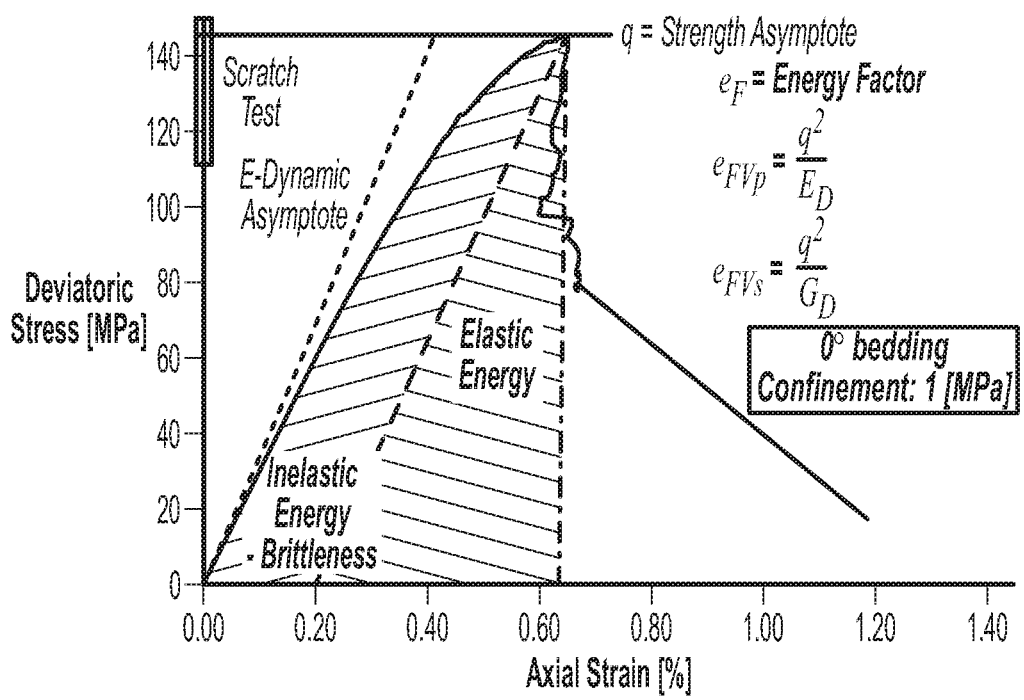

Turning to FIG. 9A, FIG. 9A illustrates a stress-strain curve in accordance with one or more embodiments. As shown in FIG. 9A, deviatoric stress is measured as a function of axial strain. Energy calculations may show a power-log linear correlation between energy factors based on the dynamic Young's modulus or Shear modulus. Thus, inelastic energy in a geological region of interest may be described in terms of a rock force profiles based on depth, length and/or a formation-type plot. Accordingly, a reservoir simulator may identify at which point various inelastic energy values remain in a brittle classification while at the same time require less energy compared to the remaining portions of a rock specimen profile. In FIG. 9A, the triaxial compression data are obtained with a bedding angle of 0° and a confining pressure of 1 MPa.

Figure 9B:
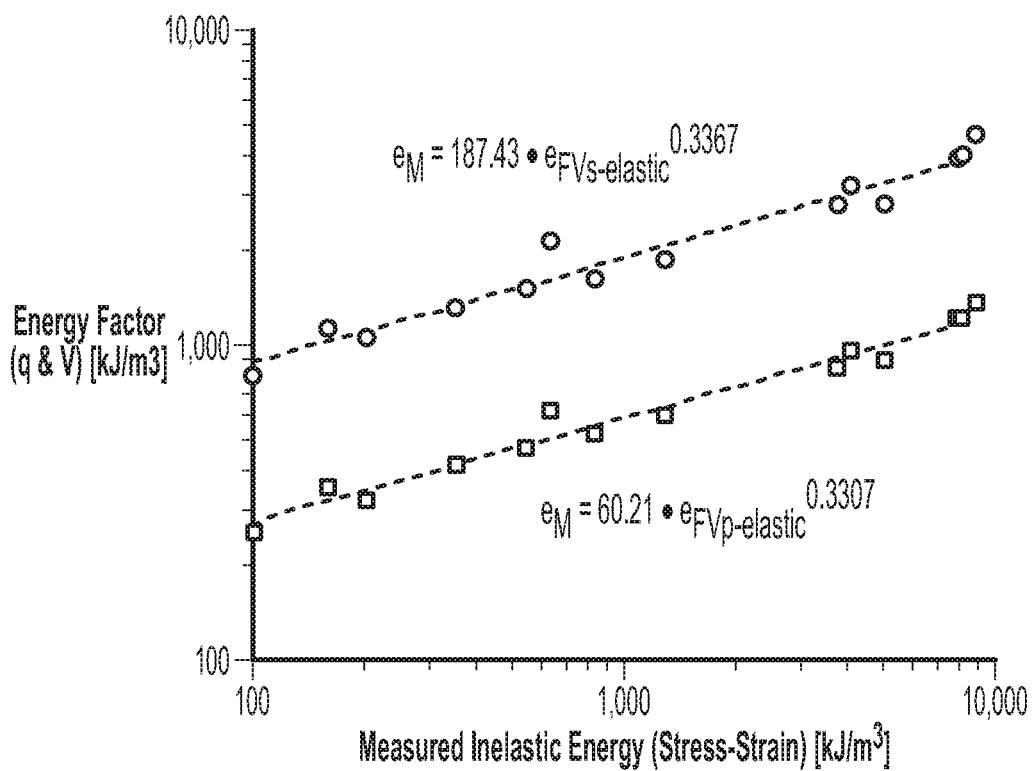

Turning to FIG. 9B, FIG. 9B shows a comparison between energy factors and inelastic energy in accordance with one or more embodiments. In FIG. 9B, measured inelastic energy is plotted with respect to energy factor values. This comparison illustrates the measured inelastic energy from stress-strain curves with the energy factor values from the scratch test and ultrasonic wave data. Thus, two sets of energy factors are illustrated, one energy factor for the dynamic Young's modulus and another set of energy factors for Shear modulus. Circles show the energy comparison using the Shear Modulus, while squares indicate the energy comparison using the dynamic Young's Modulus.

Returning to FIG. 3, in Block 350, an amount of tensile strength of a rock specimen is determined using Brazilian test data in accordance with one or more embodiments. For example, a reservoir simulator may be used to determine tensile strength and strain using Brazilian test data.

In Block 360, a geomechanical model for a geological region of interest is generated that describes various brittleness values using one or more energy factors and an amount of inelastic energy in accordance with one or more embodiments. Brittleness values may correspond to a geomechanical parameter for evaluating whether various unconventional reservoirs, such as shale gas reservoirs, can form a complex fracture network for hydrocarbon production. Certain brittleness values may correlate to the presence of hydraulically induces fractures that close slowly in comparison to geological regions with low brittleness values. As such, a reservoir simulator may perform a brittleness evaluation to generate a geomechanical model based on an analysis of rock index properties, anisotropy, non-linear elastic-plastic behavior, and associated mechanical failures. Such information for generating the geomechanical model may be based on tensile strength data, one or more energy factors, and measurements of inelastic energy within the geological region of interest. Likewise, the reservoir simulator may compute strength, stiffness, and anisotropy values for the geomechanical model in order to measure strain hardening and softening. Therefore, a geomechanical model may identify one or more brittle-ductile transition points or sweet spots for hydraulic fracturing. For more information on geomechanical models and/or brittleness values, see FIGS. 1 and 2 above and the accompanying description.

In Block 370, an injection fluid pressure is determined using a geomechanical model, an amount of tensile strength, and fracture plane roughness data in accordance with one or more embodiments. The injection fluid may be similar to the injection fluids described above in FIG. 2 and the accompanying description.

Figure 10:
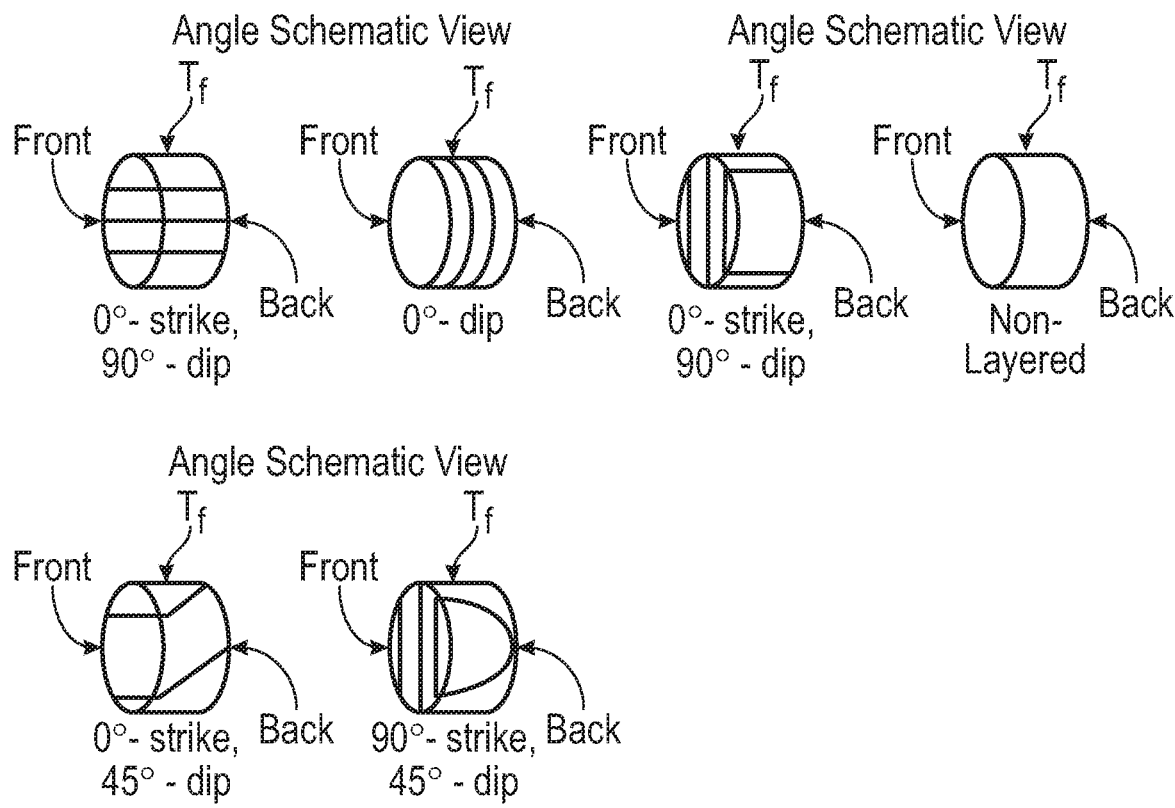

Turning to FIG. 10, FIG. 10 shows a tensile strength analysis for modeling hydraulic fracturing initiation in accordance with one or more embodiments. For example, tensile strength measurements of various layered shales rock specimens are shown with different loading conditions. More specifically, a tensile analysis is shown with the following loading conditions: (1) parallel and perpendicular loading conditions to the 90° bedding angle rock specimens (0°-strike/90°-dip and 90°-strike/90°-dip); (2) parallel loading condition to the 0° bedding angle rock specimens (0°-dip); and (3) parallel and perpendicular loading conditions to the 45° bedding angle rock specimens (0°-strike/45°-dip and 90°-strike/45°-dip). Thus, FIG. 10 provides information regarding anisotropic behavior for a geological region of interest during various tensile experiments.

Figure 11:
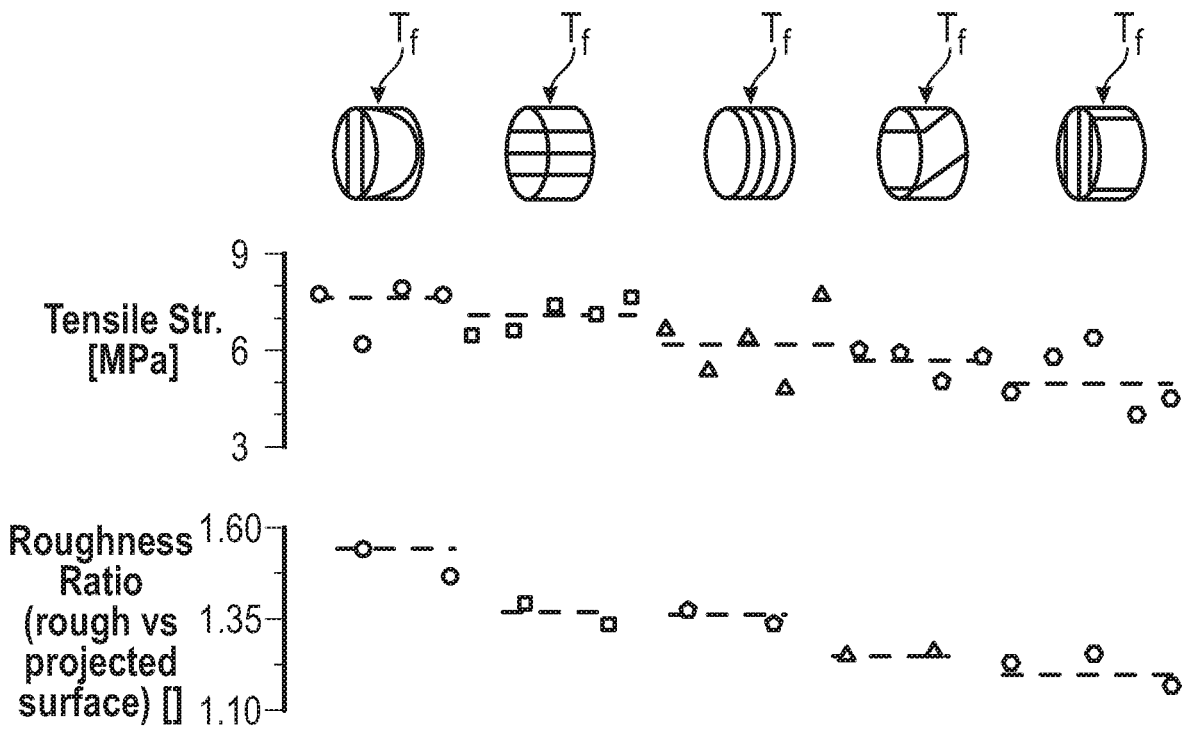

Turning to FIG. 11, FIG. 11 shows computed tensile strength and roughness ratio results for rock specimens with different bedding angle orientations in accordance with one or more embodiments. For example, tensile strength data and fracture plane roughness data may provide information regarding various intrinsic anisotropy effects with regard to the fabric and various layers of a geological region of interest. For example, the analysis in FIG. 11 may describe how tensile strength and fracture/proppant interaction occur at different bedding angle orientations. For example, a noticeable difference may be present in regard to roughness and tensile strength results with respect to different bedding angle orientations. Thus, a reservoir simulator may use these results in determining the amount of pressure for inducing hydraulic fracturing, control fracture propagation, and determine the proppant flow interaction with the fractured surface.

Returning to FIG. 3, in Block 380, a stimulation treatment is performed for a geological region of interest based on an injection fluid pressure in accordance with one or more embodiments. For more information regarding stimulation treatments, see FIG. 2 described above and the accompanying description.

Figure 12:
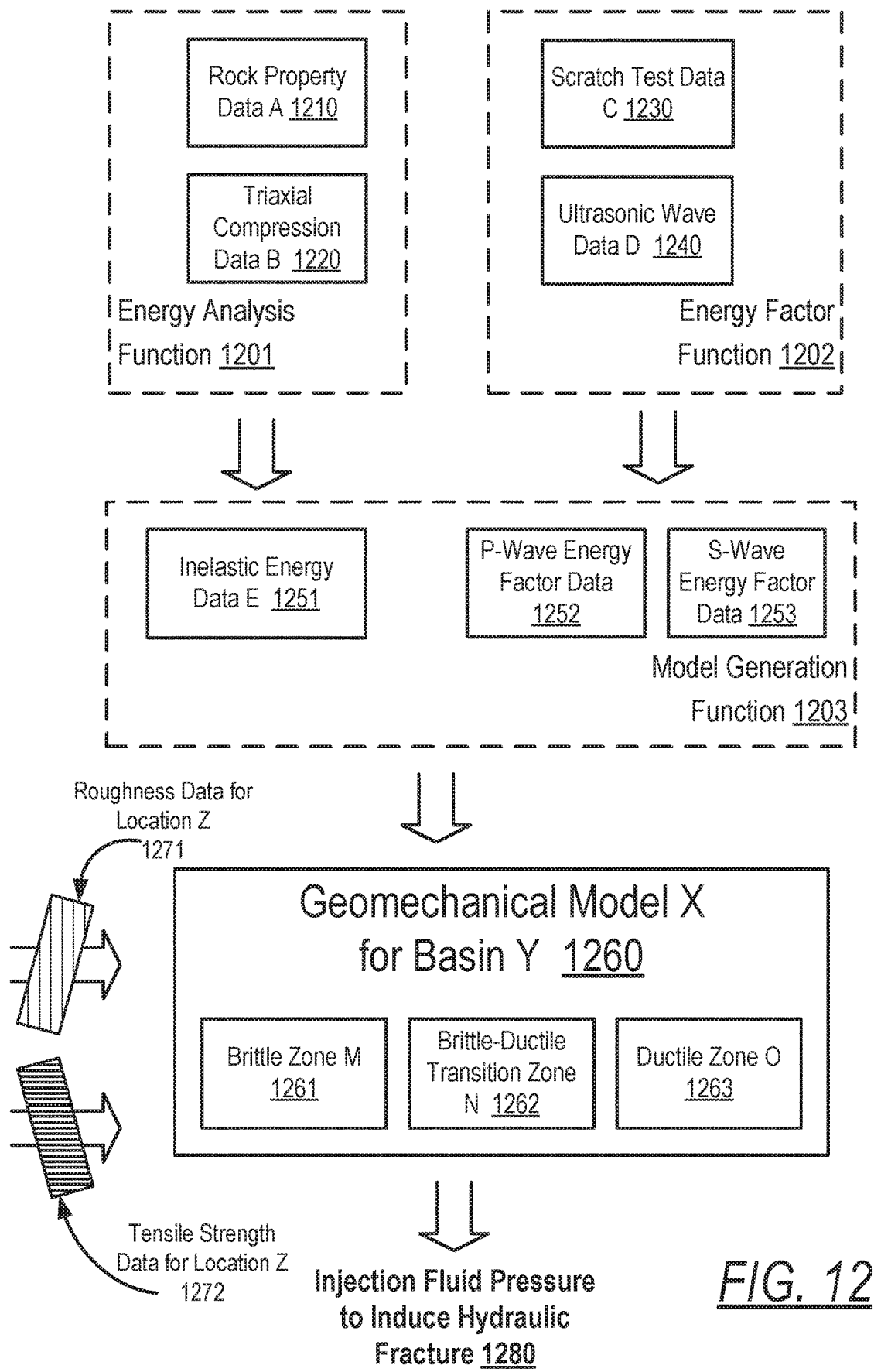

Turning to FIG. 12, FIG. 12 provides an example of generating and using a geomechanical model in accordance with one or more embodiments. The following example is for explanatory purposes only and not intended to limit the scope of the disclosed technology. In FIG. 12, FIG. 12 shows an energy analysis function (1201) and an energy factor function (1202) that are used by a reservoir simulator (not shown). With respect to the energy analysis function (1201), rock property data A (1210) and triaxial compression data B (1220) are used as inputs to determine inelastic energy data E (1251). With respect to the energy factor function (1202), scratch test data C (1230) and ultrasonic wave data D (1240) are used as inputs to determine energy factor data for p-waves and s-waves (i.e., p-wave energy factor data (1252), s-wave energy factor data (1253)).

Keeping with FIG. 12, the reservoir simulator uses inelastic energy data E (1251), p-wave energy factor data (1252), and s-wave energy factor data (1253) to generate a geomechanical model X (1260) for basin Y using a model generation function (1203). The resulting geomechanical model X (1260) includes a brittle zone M (1261), a brittle-ductile transition zone N (1262), and a ductile zone O (1263). As such, the reservoir simulator analyzes a location Z in the brittle-ductile transition zone N (1262) for a possible stimulation treatment. Accordingly, the reservoir simulator obtains roughness data (1271) for location Z and tensile strength data (1272) for location Z to determine an injection fluid pressure (1280) for an injection fluid to induce a hydraulic fracture at location Z.

Figure 13:
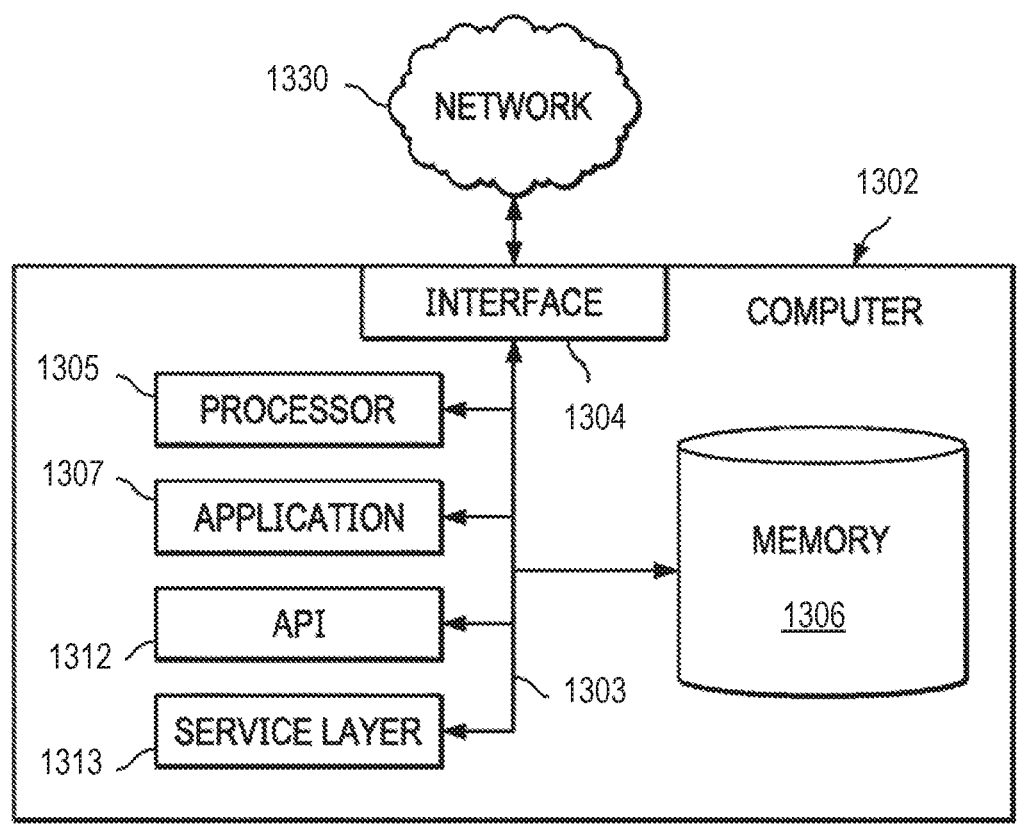
FIG. 13 shows a computer system in accordance with one or more embodiments.

Embodiments may be implemented on a computer system. FIG. 13 is a block diagram of a computer system (1302) used to provide computational functionalities associated with described algorithms, methods, functions, processes, flows, and procedures as described in the instant disclosure, according to an implementation. The illustrated computer (1302) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (1302) may include a computer that includes an input device, such as a keypad, keyboard, touch screen, or other device that can accept user information, and an output device that conveys information associated with the operation of the computer (1302), including digital data, visual, or audio information (or a combination of information), or a GUI.

The computer (1302) can serve in a role as a client, network component, a server, a database or other persistency, or any other component (or a combination of roles) of a computer system for performing the subject matter described in the instant disclosure. The illustrated computer (1302) is communicably coupled with a network (1330). In some implementations, one or more components of the computer (1302) may be configured to operate within environments, including cloud-computing-based, local, global, or other environment (or a combination of environments).

At a high level, the computer (1302) is an electronic computing device operable to receive, transmit, process, store, or manage data and information associated with the described subject matter. According to some implementations, the computer (1302) may also include or be communicably coupled with an application server, e-mail server, web server, caching server, streaming data server, business intelligence (BI) server, or other server (or a combination of servers).

The computer (1302) can receive requests over network (1330) from a client application (for example, executing on another computer (1302)) and responding to the received requests by processing the said requests in an appropriate software application. In addition, requests may also be sent to the computer (1302) from internal users (for example, from a command console or by other appropriate access method), external or third-parties, other automated applications, as well as any other appropriate entities, individuals, systems, or computers.

Each of the components of the computer (1302) can communicate using a system bus (1303). In some implementations, any or all of the components of the computer (1302), both hardware or software (or a combination of hardware and software), may interface with each other or the interface (1304) (or a combination of both) over the system bus (1303) using an application programming interface (API) (1312) or a service layer (1313) (or a combination of the API (1312) and service layer (1313). The API (1312) may include specifications for routines, data structures, and object classes. The API (1312) may be either computer-language independent or dependent and refer to a complete interface, a single function, or even a set of APIs. The service layer (1313) provides software services to the computer (1302) or other components (whether or not illustrated) that are communicably coupled to the computer (1302). The functionality of the computer (1302) may be accessible for all service consumers using this service layer. Software services, such as those provided by the service layer (1313), provide reusable, defined business functionalities through a defined interface. For example, the interface may be software written in JAVA, C++, or other suitable language providing data in extensible markup language (XML) format or other suitable format. While illustrated as an integrated component of the computer (1302), alternative implementations may illustrate the API (1312) or the service layer (1313) as stand-alone components in relation to other components of the computer (1302) or other components (whether or not illustrated) that are communicably coupled to the computer (1302). Moreover, any or all parts of the API (1312) or the service layer (1313) may be implemented as child or sub-modules of another software module, enterprise application, or hardware module without departing from the scope of this disclosure.

The computer (1302) includes an interface (1304). Although illustrated as a single interface (1304) in FIG. 13, two or more interfaces (1304) may be used according to particular needs, desires, or particular implementations of the computer (1302). The interface (1304) is used by the computer (1302) for communicating with other systems in a distributed environment that are connected to the network (1330). Generally, the interface (1304 includes logic encoded in software or hardware (or a combination of software and hardware) and operable to communicate with the network (1330). More specifically, the interface (1304) may include software supporting one or more communication protocols associated with communications such that the network (1330) or interface's hardware is operable to communicate physical signals within and outside of the illustrated computer (1302).

The computer (1302) includes at least one computer processor (1305). Although illustrated as a single computer processor (1305) in FIG. 13, two or more processors may be used according to particular needs, desires, or particular implementations of the computer (1302). Generally, the computer processor (1305) executes instructions and manipulates data to perform the operations of the computer (1302) and any algorithms, methods, functions, processes, flows, and procedures as described in the instant disclosure.

The computer (1302) also includes a memory (1306) that holds data for the computer (1302) or other components (or a combination of both) that can be connected to the network (1330). For example, memory (1306) can be a database storing data consistent with this disclosure. Although illustrated as a single memory (1306) in FIG. 13, two or more memories may be used according to particular needs, desires, or particular implementations of the computer (1302) and the described functionality. While memory (1306) is illustrated as an integral component of the computer (1302), in alternative implementations, memory (1306) can be external to the computer (1302).

The application (1307) is an algorithmic software engine providing functionality according to particular needs, desires, or particular implementations of the computer (1302), particularly with respect to functionality described in this disclosure. For example, application (1307) can serve as one or more components, modules, applications, etc. Further, although illustrated as a single application (1307), the application (1307) may be implemented as multiple applications (1307) on the computer (1302). In addition, although illustrated as integral to the computer (1302), in alternative implementations, the application (1307) can be external to the computer (1302).

There may be any number of computers (1302) associated with, or external to, a computer system containing computer (1302), each computer (1302) communicating over network (1330). Further, the term "client," "user," and other appropriate terminology may be used interchangeably as appropriate without departing from the scope of this disclosure. Moreover, this disclosure contemplates that many users may use one computer (1302), or that one user may use multiple computers (1302).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed:

1. A method, comprising:
    determining, by a computer processor, an energy factor based on scratch test data and ultrasonic wave data regarding a geological region of interest;
    determining, by the computer processor, an amount of inelastic energy regarding the geological region of interest using triaxial compression data and rock property data;
    determining, by the computer processor, one or more tensile strengths regarding the geological region of interest using Brazilian test data;
    generating, by the computer processor, a geomechanical model regarding the geological region of interest using the energy factor and the amount of inelastic energy, wherein the geomechanical model comprises a plurality of brittleness values for the geological region of interest;
    acquiring, using a profilometer scanner based on white light interferometry, fracture plane roughness data, wherein the fracture plane roughness data comprise a surface roughness of a rock specimen that identifies surface deviations in a predetermined direction; and
    determining, by the computer processor, an injection fluid pressure to induce a hydraulic fracture at a predetermined location in the geological region of interest using the geomechanical model, the one or more tensile strengths, and the fracture plane roughness data.

2. The method of claim 1, further comprising:
    determining, using the fracture plane roughness data and the geomechanical model, a proppant-flow interaction with one or more fractures in the geological region of interest,
    wherein the proppant-flow interaction corresponds to a distribution of proppant and a proppant-carrying injection fluid within the one or more fractures.

3. The method of claim 1, further comprising:
    determining, using the geomechanical model and the fracture plane roughness data, a stimulation treatment for one or more fractures in the geological region of interest, wherein the stimulation treatment comprises the injection fluid pressure and a predetermined type of proppant; and
    performing the stimulation treatment in a wellbore.

4. The method of claim 1,
    wherein the triaxial compression data describe rock mechanical behavior of the geological region of interest at a plurality of bedding angles and a plurality of confining pressures,
    wherein the triaxial compression data are acquired from a plurality of rock specimens using a triaxial cell in a laboratory.

5. The method of claim 1,
    wherein the rock property data comprise mineralogy data, total organic carbon data, damage data, porosity data, and pore size distribution data regarding the geological region of interest, and
    wherein the method further comprises:
        acquiring the mineralogy data using an x-ray diffraction or energy-dispersive x-ray spectroscopy,
        acquiring the total organic carbon data using an elemental analyzer of carbon, hydrogen, nitrogen, sulfur, and oxygen,
        measuring the damage data using a computerized tomography scan,
        acquiring the porosity data using a helium porosimeter, and acquiring the pore size distribution data using a mercury injection capillary pressure or gas adsorption technique.

6. The method of claim 1,
wherein the ultrasonic wave data are based on a plurality of p-wave measurements and a plurality of s-wave measurements acquired in a wellbore, and
wherein the plurality of p-wave measurements and the plurality of s-wave measurements are analyzed using Coda Wave interferometry.

7. The method of claim 1,
wherein the triaxial compression data comprise a stress-strain curve, and
wherein the amount of inelastic energy corresponds to a total energy minus an elastic energy below the stress-strain curve before a peak stress threshold, and
wherein the plurality of brittleness values corresponds to the inelastic energy separate from elastic energy in the stress-strain curve.

8. The method of claim 1,
wherein the scratch test data comprise a plurality of peak strength values that are based on one or more core specimens from a wellbore or from within a wellbore directly, and
wherein the scratch test data describe a force distribution of the geological region of interest.

9. The method of claim 1,
wherein the Brazilian test data comprise tensile strength calculations based on a disc-shaped specimen of rock that is loaded by opposing loads at a periphery of the disc-shaped specimen, and
wherein force of the opposing loads is increased at a predetermined rate until a rock failure of the disc-shaped specimen occurs.

10. A system, comprising:
a logging system coupled to a plurality of logging tools;
a drilling system coupled to the logging system; and
a reservoir simulator comprising a computer processor, wherein the reservoir simulator is coupled to the logging system and the drilling system, the reservoir simulator comprising functionality for:
  determining an energy factor based on scratch test data and ultrasonic wave data regarding a geological region of interest;
  determining an amount of inelastic energy regarding the geological region of interest using triaxial compression data and rock property data;
  determining one or more tensile strengths regarding the geological region of interest using Brazilian test data;
  generating a geomechanical model regarding the geological region of interest using the energy factor and the amount of inelastic energy, wherein the geomechanical model comprises a plurality of brittleness values for the geological region of interest;
  obtaining, based on white light interferometry, fracture plane roughness data, wherein the fracture plane roughness data comprise a surface roughness of a rock specimen that identifies surface deviations in a predetermined direction; and
  determining an injection fluid pressure to induce a hydraulic fracture at a predetermined location in the geological region of interest using the geomechanical model, the one or more tensile strengths, and the fracture plane roughness data.

11. The system of claim 10,
wherein the plurality of logging tools comprises a scratcher tool that performs scratch test at a predetermined depth interval, and
wherein the scratch test data corresponds to a well log that is generated by the scratcher tool.

12. The system of claim 10, further comprising:
a control system coupled to the reservoir simulator,
wherein the reservoir simulator further comprises functionality for determining, using the geomechanical model and the fracture plane roughness data, a stimulation treatment for one or more fractures in the geological region of interest, wherein the stimulation treatment comprises the injection fluid pressure and a predetermined type of proppant, and
wherein the control system comprises functionality for performing the stimulation treatment in a wellbore.

13. The system of claim 10,
wherein the ultrasonic wave data are based on a plurality of p-wave measurements and a plurality of s-wave measurements acquired in a wellbore, and
wherein the plurality of p-wave measurements and the plurality of s-wave measurements are analyzed using Coda Wave interferometry and the reservoir simulator.

14. The system of claim 10,
wherein the triaxial compression data comprise a stress-strain curve, and
wherein the amount of inelastic energy corresponds to a total energy minus an elastic energy below the stress-strain curve before a peak stress threshold, and
wherein the plurality of brittleness values corresponds to the inelastic energy separate from elastic energy in the stress-strain curve.

* * * * *